US005712384A

United States Patent [19]
Symonds et al.

[11] Patent Number: 5,712,384
[45] Date of Patent: Jan. 27, 1998

[54] RIBOZYMES TARGETING RETROVIRAL PACKAGING SEQUENCE EXPRESSION CONSTRUCTS AND RECOMBINANT RETROVIRUSES CONTAINING SUCH CONSTRUCTS

[75] Inventors: Geoffrey P. Symonds, Rose Bay; Lun-Quan Sun, Ryde, both of Australia

[73] Assignee: Gene Shears Pty Ltd., North Ryde, Australia

[21] Appl. No.: 178,082

[22] Filed: Jan. 5, 1994

[51] Int. Cl.⁶ .......................... C12Q 1/68; C07H 21/04; A61K 48/00
[52] U.S. Cl. .................. 536/24.5; 536/23.1; 536/23.2; 435/6; 435/91.31; 435/240.2; 435/320.1; 514/44
[58] Field of Search .................. 435/91.31, 6, 172.3, 435/240.2, 252.3, 320.1; 514/44; 536/23.1, 23.2, 24.5

[56] References Cited

FOREIGN PATENT DOCUMENTS 9217211 10/1992 WIPO.

OTHER PUBLICATIONS

Barinaga, Science 262:1512 (1993).
Donahue et al. J.V.r. 62:722 (1988).
Olmsted et al. PNAS 86:8088 (1989).
Johnston et al. Science 260: 1286, (1993).
Han et al. PNAS 88:4313 (1991).
Aropulic et al. J.V.r. 66:1432 (1992).
Ratner et al. Nature 313:277 (1985).
Goodchild et al. NAR 20:4607 (1992).
Lever et al. J.V.r. 63:4085 (1989).
Mann et al. J. V.r. 54: 401 (1985).
Stull et al. Pharm. Res. 12: 465 (1995).
Berzal-Herranz, A. et al. (1993) "Essential Nucleotide Sequences and Secondary Structure Elements of the Hairpin Ribozyme," EMBO 12:2567–2674 (Exhibit 3).
Bevec, D. et al. (1992) "Inhibition of Human Immunodeficiency Virus Type 1 Replication in Human T Cells by Retroviral–Mediated Gene Transfer of a Dominant–Negative Rev Trans–Activator," Proc. Natl. Acad. Sci. (USA) 89:9870–9874 (Exhibit 4).
Bischofberger, N. and Wagner, R.W. (1992) "Antisense Approaches to Antiviral Agents," Virology 3:57–66 (Exhibit 5).
Chen, C–J. et al. (1992) "Inhibition of HIV–1 Replication by Novel Multitarget Ribozymes," Ann. N.Y. Acad. Sci. (USA) 660:271–273 (Exhibit 6).
Chen, C–J. et al. (1992) "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," Nucleic Acids Res. (Eng.) 20:4581–4589 (Exhibit 7).
Chowrira, B.M. et al. (1993) "Four Ribose 2'–Hydroxyl Groups Essential for Catalytic Function of the Hairpin Ribozyme," J.Biol.Chem. 268:19458–19462 (Exhibit 8).

Cournoyer, D. and Caskey, C.T. (1993) "Gene Therapy of the Immune System," Annu. Rev. Immunol. (USA) 11:297–329 (Exhibit 9).
Crisell, P. et al. (1993) "Inhibition of HIV–1 Replication by Ribozymes that Show Poor Activity in vitro," Nucleic Acids Res. (Eng.) 21:5251–5255 (Exhibit 10).
Dropulic, B. et al. (1993) "Ribozymes: Use As Anti–HIV Therapeutic Molecules," Antisense Res. Dev. (USA) 3:87–94 (Exhibit 11).
Goodchild, J. (1991) "Antisense Antivirals," Antisense Res. Dev. (USA) 1: 361–364 (Exhibit 12).
Heidenreich, O. and Eckstein, F. (1992) "Hammerhead Ribozyme–Mediated Cleavage of Long Terminal Repeat RNA of Human Immundeficiency Virus Type 1," J. Biol. Chem. (USA) 267:1904–1909 (Exhibit 13).
Homann, M. et al. (1993) "Incorporation of the Catalytic Domain of a Hammerhead Ribozyme Into Antisense RNA Enhances Its Inhibitory Effect on the Replication of Human Immunodeficiency Virus Type 1," Nucleic Acids Res. (Eng.) 21:2809–2814 (Exhibit 14).
Johnston, M.I. and Burke, J.M. (1993) "Present Status and Future Prospects for HIV Therapies," Science 260:1286–1293 (Exhibit 15).
Joseph, S. et al. (1993) "Optimization of an Anti–Hairpin Ribozyme by in Vitro Selection," J. Biol. Chem. (USA) 268:24515–24518 (Exhibit 16).
Joseph, S. et al. (1993) "Substrate Selection Rules for the Hairpin Ribozyme Determined by in Vitro Selection, Mutation, and Analysis of Mismatched Substrates," Genes and Development 7:130–138 (Exhibit 17).
Levy, J. (1993) "Pathogenesis of Human Immunodeficiency Virus Infection," Microbiol. Rev. 57:183–289 (Exhibit 18).

(List continued on next page.)

*Primary Examiner*—John LeGuyader
*Attorney, Agent, or Firm*—John P. White

[57] ABSTRACT

This invention is directed to a synthetic non-naturally occurring oligonucleotide compound which comprises nucleotides whose sequence defines a conserved catalytic region and nucleotides whose sequence is capable of hybridizing with a predetermined target sequence within a packaging sequence of an RNA virus. Preferably, the viral packaging sequence is a retrovirus packaging sequence or the HIV-1 Psi packaging sequence. The RNA virus may be HIV-1, Feline Leukemia Virus, Feline Immunodeficiency Virus or one of the viruses listed in Table I. The conserved catalytic region may be derived from a hammerhead ribozyme, a hairpin ribozyme, a hepatitis delta ribozyme, an RNAase P ribozyme, a group I intron, a group II intron. The invention is also directed to multiple ribozymes, combinations of ribozymes, with or without antisense, and combinations of ribozymes, with antisense, and TAR decoys, poly TARs or RRE decoys targeted against the RNA virus and combinations of ribozymes and antisense targetted against the RNA virus. Vectors are also described. Further, methods of treatment and methods of use both in vivo and ex vivo are described.

8 Claims, 11 Drawing Sheets

OTHER PUBLICATIONS

Lisziewicz, J. et al. (1993) "Inhibition of Human Immunodeficiency Virus Type 1 Replication By Regulated Expression of a Polymeric Tat Activation Response RNA Decoy as a Strategy For Gene Therapy in AIDS," Proc. Natl. Acad. Sci. USA 90: 8000–8004 (Exhibit 19).

Liu, J.et al. (1994) "Regulated Expression of a Dominant Negative Form of Rev Improves Resistance to HIV Replication in T Cells," Gene Therapy (Eng.) 1:32–37 (Exhibit 20).

Lo, K.M. et al. (1992) "Inhibition of Replication of HIV–1 by Retroviral Vectors Expressing tat–Antisense and Anti–tat Ribozyme RNA," Virology (USA) 190:176–183 (Exhibit 21).

Lori, F. et al. (1994) "Rapid Protection Against Human Immunodeficiency Virus Type 1 (HIV–1) Replication Mediated by High Efficiency Non–retroviral Delivery of Genes Interfering with HIV–1 tat and gag," Gene Therapy (Eng.) 1:27–31 (Exhibit 22).

Ohkawa, J. et al. (1993) "Importance of Independence in Ribozyme Reactions: Kinetic Behavior of Trimmed and of Simply Connected Multiple Ribozymes with Potential Activity Against Human Immunodeficiency Virus," Proc. Natl. Acad. Sci. USA 90:11302–11306 (Exhibit 23).

Ohkawa, J. et al. (1993) "Multiple Site–Specific Cleavage of HIV RNA by Transcribed Ribozymes from Shotgun–Type Trimming Plasmid," Nucleic Acids Symp. Ser. (Eng.) 29:121–122 (Exhibit 24).

Ojwang, J.O. et al. (1992) "Inhibition of Human Immunodeficiency Virus Type 1 Expression by a Hairpin Ribozyme," Proc. Natl. Acad. Sci. USA 89:10802–10806 (Exhibit 25).

Rossi, J.J. et al. (1992) "Catalytic Antisense RNA (Ribozymes): Their Potential and Use as Anti–HIV–1 Therapeutic Agents," Adv. Exp. Med. Biol. (USA) 312:95–109 (Exhibit 26).

Rossi, J.J. et al. (1992) "Ribozymes as Anti–HIV–1 Therapeutic Agents: Principles, Applications, and Problems," AIDS Res. Hum. Retroviruses (USA) 8:183–189 (Exhibit 27).

Rossi, J.J. et al. (1990) "Ribozymes as Therapies for AIDS," Ann. N.Y. Acad. Sci. (USA) 616:184–200 (Exhibit 28).

Sarver, N. (1991) "Ribozymes: A New Frontier in Anti–HIV Strategy," Antisense Res. Dev. (USA) 1:373–378 (Exhibit 29).

Sarver, N. et al. (1990) "Ribozymes as Potential Anti–HIV–1 Therapeutic Agents," Science 247:1222–1225 (Exhibit 30).

Shimayama, T. et al. (1993) "Cleavage of the Highly Conserved Hairpin–Loop Region of HIV–1 by Synthetic Ribozymes," Nucleic Acids Symp. Ser. (Eng.) 29:177–178 (Exhibit 31).

Taylor, N.R. and Rossi, J.J. (1991) "Ribozyme–Mediated Cleavage of a HIV–1 gag RNA: The Effects of Nontargeted Sequences and Secondary Structure on Ribozyme Cleavage Activity," Antisense Res. Dev. 1:173–186 (Exhibit 32).

Thill, G. et al. (1993) "Structural and Sequence Elements Required for the Self–Cleaving Activity of the Hepatitis Delta Virus Ribozyme," Biochemistry 32:4254–4262 (Exhibit 33).

Weerasinghe, M. et al. (1991) "Resistance to Human Immunodeficiency Virus Type 1 (HIV–1) Infection in Human $CD4^+$ Lymphocyte–Derived Cell Lines Conferred by Using Retroviral Vectors Expressing an HIV–1 RNA–Specific Ribozyme," J. Virol (USA) 65: 5531–5534 (Exhibit 34).

Yamada, O. et al. (1994) "Intracellular Immunization of Human T Cells with a Hairpin Ribozyme Against Human Immunodeficiency Virus Type 1," Gene Therapy (Eng.) 1:38–45 (Exhibit 35).

Yu, M. et al. (1993) "A Hairpin Ribozyme Inhibits Expression of Diverse Strains of Human Immunodeficiency Virus Type 1," Proc. Natl.Acad.Sci. USA 90:6340–6344 (Exhibit 36).

Zaia, J.A. et al. (1992) "Status of Ribozyme and Antisense–Based Developmental Approaches for Anti–HIV–1 Therapy," Ann N.Y. Acad. Sci (USA) 660:95–106 (Exhibit 37).

MOLONEY MURINE LEUKEMIA VIRUS

ANTI-HIV RIBOZYME (ψ SITE)

RIBOZYMES TARGETING RETROVIRAL PACKAGING SEQUENCE EXPRESSION CONSTRUCTS AND RECOMBINANT RETROVIRUSES CONTAINING SUCH CONSTRUCTS

Throughout this application various publications are referred to by author and year within brackets. The full references are listed alphabetically after the Experimental Section. The disclosures for these publications in their entireties are hereby incorporated by reference into this application to more fully describe the state of the art to which this invention pertains.

BACKGROUND OF THE INVENTION

RETROVIRUSES

Retroviruses are viruses with RNA as their genomic material. They use host cells for their replication by stably integrating a cDNA copy of their genomic RNA into the host cell genome (Miller, 1992, and Brown, 1987). The viral genome consists of a Long Terminal Repeat (LTR) at each end (5' and 3') of the proviral cDNA form of the virus. Proceeding from 5' to 3', the LTR consists of U3 and U5 sequences linked by a short sequence termed R. Transcription commences within the 5' LTR and terminates at a polyadenylation site within the 3' LTR. Adjacent to the LTRs are short sequences necessary for priming of positive and negative strand DNA synthesis by reverse transcriptase. Splice donor and acceptor sequences are also present within the genome and these are involved in the production of sub-genomic RNA species. Directly proximal to the 5' LTR is a sequence necessary for the encapsidation of viral RNA into virions. This is termed the Psi packaging sequence. It is an essential and specific signal ensuring that the viral RNA is packaged. The bulk of the viral RNA consists of the gag, pol and env replicarive genes which encode, respectively, core proteins (gag), the enzymes integrase, protease and reverse transcriptase (pol), and envelope proteins (env).

Retroviral infection of a cell is initiated by the interaction of viral glycoproteins with cellular receptors (A) (see FIG. 1). Following adsorption and uncoating, the viral RNA enters the target cell and is converted into cDNA by the action of reverse transcriptase, an enzyme brought within the virion (B). The cDNA adopts a circular form (C), is converted to double-stranded cDNA and then becomes integrated into the host cell's genomic DNA by the action of integrase (D). Once integrated, proviral cDNA is transcribed from the promoter within the 5' LTR (E). The transcribed RNA either acts as mRNA and is translated to produce the viral proteins (F) or is left as nascent viral RNA. This viral RNA contains a Psi packaging sequence which is essential for its packaging into virions (G). Once the virion is produced, it is released from the cell by budding from the plasma membrane (H). In general, retroviruses do not cause lysis of the host cell; HIV is an exception to this. The proviral cDNA remains stably integrated in the host genome and is replicated with the host DNA so that progeny cells also inherit the provirus. Potential anti-viral agents may be targeted at any of these replicative control points.

HUMAN IMMUNODEFICIENCY VIRUS (HIV)

HIV belongs to the class retrovirus and its replication is as outlined above. The entry of HIV into cells, including T lymphocytes, monocytes and macrophages, is generally effected by the interaction of the gp120 envelope protein of HIV with a CD4 receptor on the target cell surface. The amino acid sequence of gp120 can be highly variable in different patients (or even the same patient) making vaccine production very difficult (Brown, 1987 and Peterlin et al., 1988). This variability appears to be associated with disease progression. The major peculiarities for HIV are i) that (as for other members of the group lentivirus) it has a latent phase in which the provirus may lie dormant following integration into the host cell's genome, and ii) it is cytopathic for T lymphocyte target cells. HIV commences replication after cells which harbor the provirus are activated. The stimulus (or stimuli) for cell activation and accompanying viral replication have not yet been clearly identified (Brown, 1987 and Peterlin et al., 1988). As for all retroviruses, gag, pol and env gene products are translated into structural and enzymatic proteins. In the case of HIV, there are additional regulatory genes. Specifically, tat and rev gene products are translated into regulatory proteins and act as transcriptional enhancers to induce high levels of gene expression. Nef is another regulatory gene which serves to modulate viral replication levels (Jones, 1989, Greene, 1990, and Epstein, 1991).

HIV replication is highest in activated and proliferating cells; cellular activation leads to the binding of nuclear transcription and cellular enhancer factors to the HIV LTR which results in increased levels of transcription. As for all retroviruses, the packaging region (Psi) is a cis-acting RNA sequence present on the HIV genome, necessary for encapsidation of the genomic RNA. The formation of a core incorporating gag proteins, pol enzymes and viral RNA is the last stage of the HIV replication cycle. This core obtains a membrane and leaves the cell by budding through the cell membrane (Peterlit et al., 1988, Jones, K. A., 1989, Greene, 1990, and Epstein, 1991).

To date, a number of agents for the suppression of HIV replication have been studied. a description follows of certain agents that have been targeted at the replicative stages represented in FIG. 1.

(A) Viral Adsorption to the Target Cell

Soluble CD4 has been used in an attempt to occupy a high proportion of the viral receptors so that the virus is unable to bind to the cell membrane. However, to date this has not been found to be a successful therapeutic strategy (Stevenson et al., 1992). Sulphated polysaccharides have demonstrated an ability to inhibit HIV infection possibly by interrupting cell-virus fusion (McClure et al., 1992). Antibodies to HIV itself, the host cell receptors or HIV envelope determinants as well as CD4 conjugated exotoxin (Stevenson et al., 1992) are other possible methods of interrupting viral entry into a cell.

(B) Production of cDNA by Reverse Transcriptase

Chemicals such as azidothymidine triphosphate (AZT) have been found to inhibit reverse transcriptase in vitro. AZT is presently administered both routinely to AIDS patients and when they receive bone marrow transplants, the latter in an attempt to protect the normal marrow from residual HIV (Miller, 1992).

(C) Translocation of the cDNA from the Cytoplasma to the Nucleus

It may be possible to interrupt cDNA translocation across nuclear pores or nuclear transport itself but this has not yet been shown to be successful.

(D) Integration of the cDNA into the Host Genome

It may also be possible to block the integration of the proviral cDNA into the host cell genome (Stevenson et al., 1992). To date, there are no candidate compounds which have proven effective.

(E) Proviral Transcription 5,6-dichloro-1-beta-D-ribofuranosyl benzimidazole is known to interfere with transcriptional elongation (Stevenson et al., 1992). Sense TAR analogs may also affect transcription by binding the tat protein thereby inhibiting its ability to activate HIV (Miller, 1992 and Sullenger et al., 1990).

(F) Translation of HIV mRNA

Antisense RNA, by binding to viral RNA, may inhibit viral replication (Sczakiel et al., 1992). Binding to mRNA may serve to inhibit translation; binding to the nascent viral RNA may also act to inhibit productive packaging of RNA into virions.

(G) Viral Packaging and Production of Mature Virions

Protease induces specific cleavage of the HIV polyprotein. This activity is essential for production of mature, infectious virions. Several compounds such as α,α-difluoroketones, have been found to inhibit HIV protease and have shown a degree of anti-viral activity in tissue culture. However, most protease inhibitors have displayed short serum half-life, rapid biliaryclearance and poor oral availability (Debouck, 1992).

RIBOZYMES

Ribozymes are enzymatic RNAs that cleave RNA and exhibit turnover. In some classes of ribozymes by the addition of complementary sequence arms, they can be rendered capable of pairing with a specific target RNA and inducing cleavage at specific sites along the phosphodiester backbone of RNA (Haseloff et al., 1988; Rossi et al., 1992; Hampel, 1990; Ojwang, 1992). The hammerhead ribozyme is small, simple and has an ability to maintain site-specific cleavage when incorporated into a variety of flanking sequence motifs (Haseloff et al., 1988; Rossi et al., 1992). These features make it particularly well suited for gene suppression.

SUMMARY OF THE INVENTION

This invention is directed to a synthetic non-naturally occurring oligonucleonide compound which comprises nucleotides whose sequence defines a conserved catalytic region and nucleotides whose sequence is capable of hybridizing with a predetermined target sequence within a packaging sequence of an RNA virus. Preferably, the viral packaging sequence is a retrovirus packaging sequence and in one embodiment the HIV-1 Psi packaging sequence. The RNA virus may be HIV-1, Feline Leukemia Virus, Feline Immunodeficiency Virus or one of the viruses listed in Table I. The conserved catalytic region may be derived from a hammerhead ribozyme, a hairpin ribozyme, a hepatitis delta ribozyme, an RNAase P ribozyme, a group I intron, a group II intron. The invention is also directed to multiple ribozymes, and combinations of ribozymes and antisense or ribozymes with or without antisense and polyTAR, RRE or TAR decoys targeted against the RNA virus. Vectors are also described. Further, methods of treatment and methods of use both in vivo and ex vivo are described.

The standard expression constructs were based on pSV2neo and consisted of the SV40 promoter upstream of the $neo^r$ gene with one of the designed ribozymes or an antisense sequence complementary to the Psi packaging sequence (anti-Psi) inserted into the Sma I site of $neo^r$.

Figure 5:
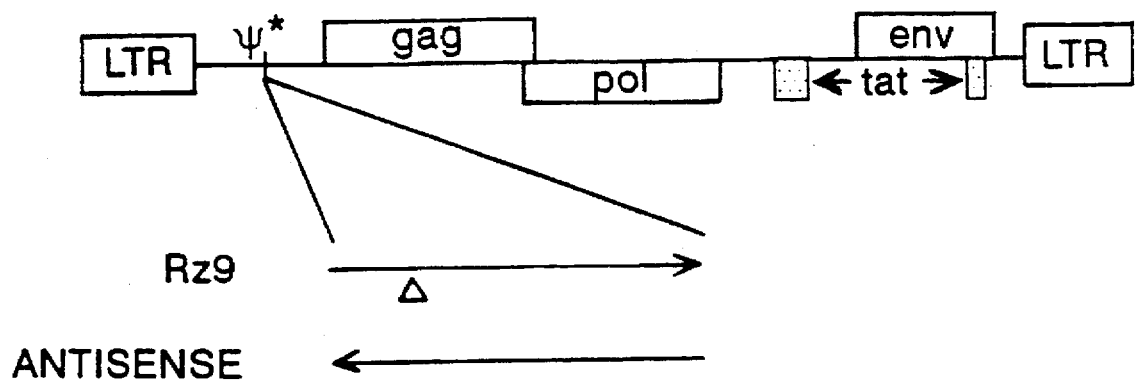

FIG. 5. HIV Packaging Site Targeted The figure shows a simplified view of the HIV genome with ribozyme 9 being targeted to a sequence within the Psi packaging site.

Figure 6:
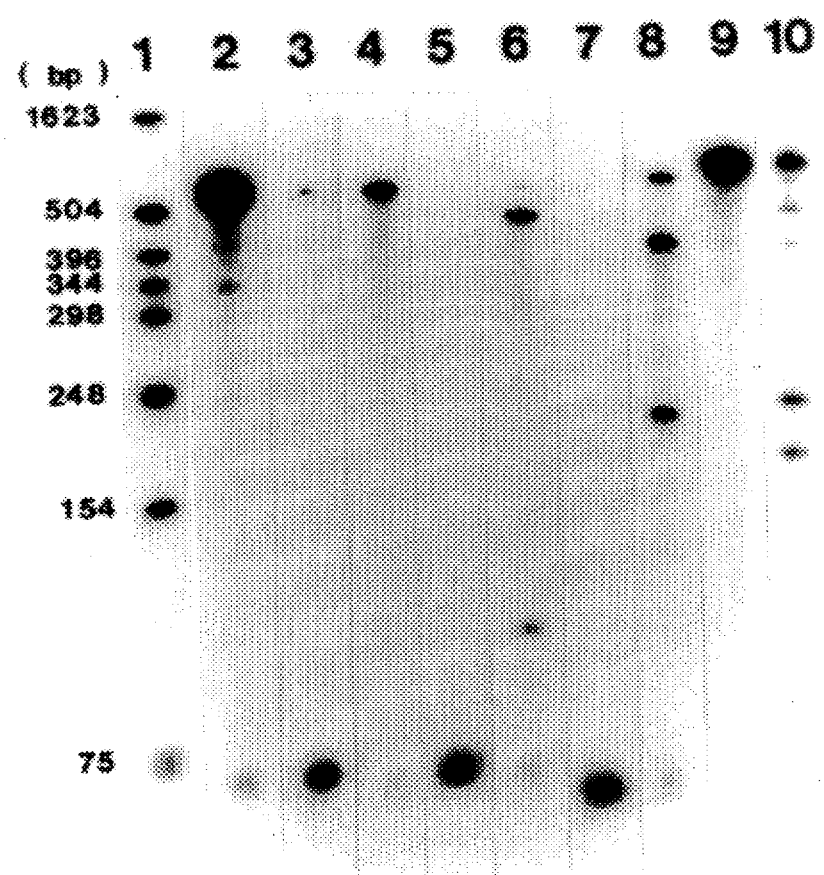

FIG. 6. In vitro cleavage of in vitro generated Mo-MLV packaging region RNA by ribozymes. Lane 1 is pBR322 marker DNA digested with HinfI. Lane 2 is the approximately 550 kb substrate. Lanes 3, 5, 7 and 9 were the in vitro generated Rz243, Rz274, Rz366 and Rz-M7 alone. The following ribozymes were added to target substrate RNA: lane 4, Rz243; lane 6, Rz274; lane 8, Rz366; lane 10, Rz-M7. The cleavage reactions were carried out at 37° C. for 30 min in 10 mM $MgCl_2$, 50 mM Tris.Cl, pH 7.5 after the samples were heated at 80° C. for 2 min in 10 mM Tris.Cl, pH 7.5.

Figure 7:
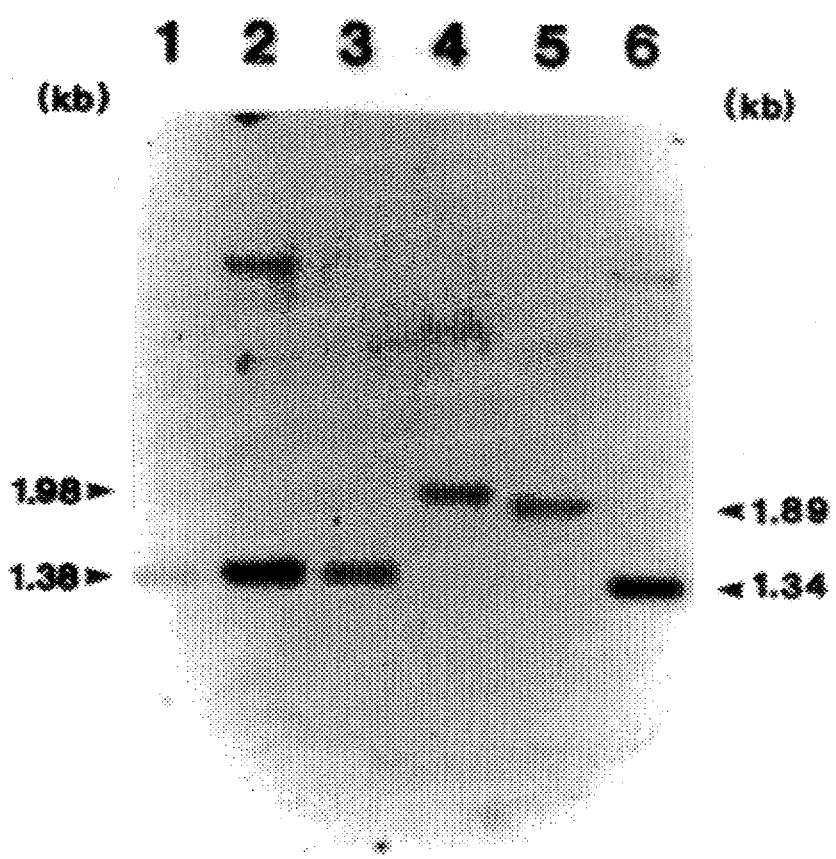

FIG. 7. Southern hybridization of DNA from the ribozyme or antisense construct-transfected cell lines. Genomic DNA (10 μg) from 3T3-Mo-MLV cells transfected with the various constructs: lane 1, pSV243; lane 2, pSV274; lane 3, pSV366; lane 4, pSV-MT; lane 5, pSVAs-Psi; and lane 6, pSV2neo vector alone were digested with HindIII/NruI, separated on a 0.6% agarose gel, blotted onto nitrocellulose filter and hybridized with the $^{32}P$-labelled $neo^r$ gene probe. Arrowheads indicate the predicted size of the $neo^r$ gene alone (1.34 kb) and the $neo^r$ gene plus the single ribozymes (1.38 kb), plus a multiple Rz (1.98 kb), or plus antisense (1.89 kb).

Figure 8:
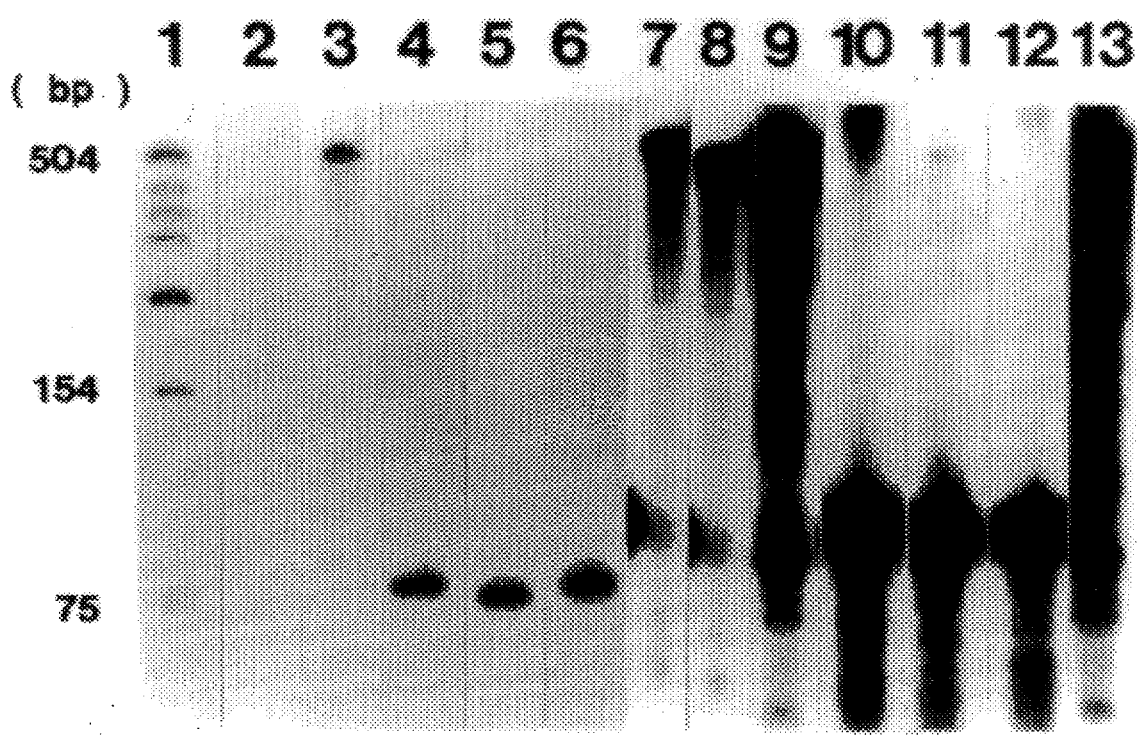

FIG. 8. RNase protection analysis to study ribozyme/antisense constructs expression. 20 μg total RNA from a series of transfected cells was analyzed for expression of the ribozymes or antisense constructs using $^{32}P$-labelled riboprobes. Lane 1, size marker end labelled DNA fragments of pBR322 digested with HinfI; lane 2, riboprobe of RzM7 hybridized with yeast RNA and digested with RNase; lane 3, riboprobe of RzM7 hybridized with yeast RNA, followed by no RNase digestion; lanes 4–8, riboprobes of Rz243, Rz274, Rz366, RzM7 and As-Psi hybridized with RNA from pSV243, pSV274, pSV366, pSV-M7 and pSVAs-Psi transfected cells respectively, and digested with RNase; lanes 9–13, riboprobes of RzM7, Rz243, Rz274, Rz366 and As-Psi only. One clone for each construct which showed the best suppression of Mo-MLV replication was used in the assay.

Figure 9:
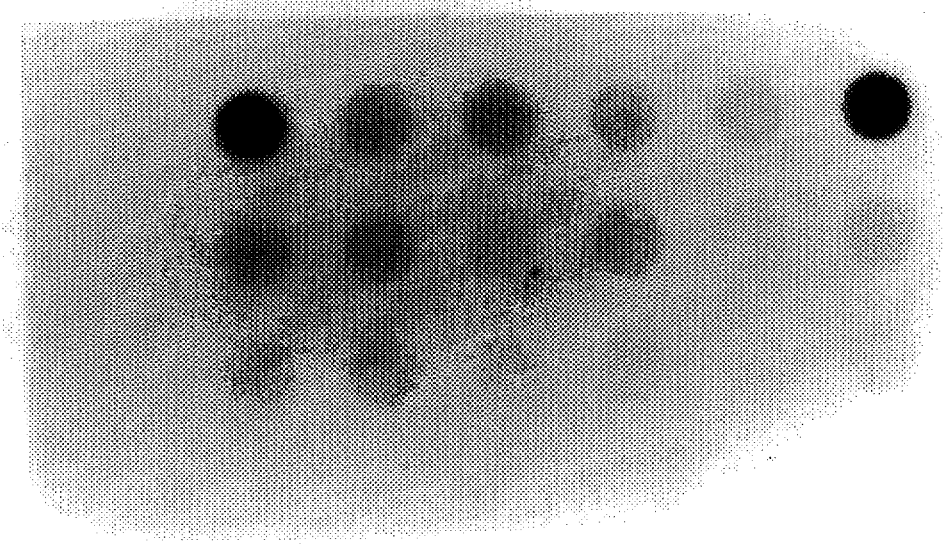

FIG. 9. Autoradiograph of a dot blot of viral RNA derived from different Mo-MLV-producing 3T3 cells. Viral RNA preparations at 1:1, 1:5 and 1:10 dilutions were probed with a $^{32}$P-labelled riboprobe complementary to Mo-MLV Psi packaging region as described previously. Lane 1, yeast RNA; lanes 2–7, RNA from supernatants of 3T3-Mo-MLV cells transfected with pSV243, pSV274, pSV366, pSV-M7, pSVAsPsi and pSV2neo. It can be seen that viral RNA levels are lowered by the ribozymes effective in cleaving RNA target molecules in vitro and by the antisense.

Figure 10:
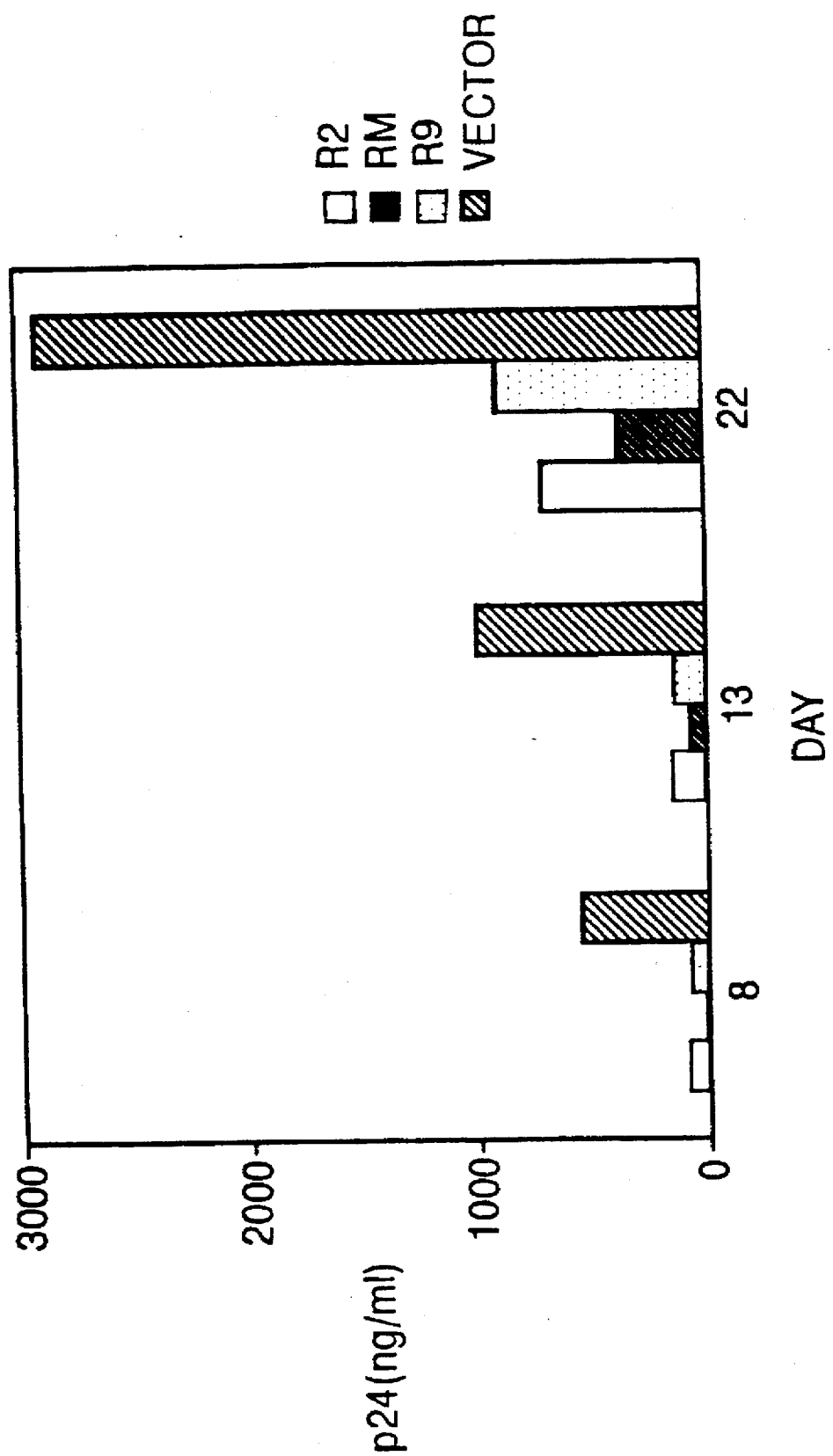

FIG. 10. p24 levels in long term assay The histogram chart shows data for HIV replication as measured by p24 levels at days 8,13 and 22 for ribozyme 9(Rz-9), the ribozyme construct targeted to the HIV packaging site. Vector, is the control construct. Rz-2 and Rz-M are two ribozyme constructs targeted to the tat gene of HIV. Rz-M is a multi-ribozyme containing several ribozymes targeted to different sites within tat. This includes the site targeted by Rz-2.

Figure 11:
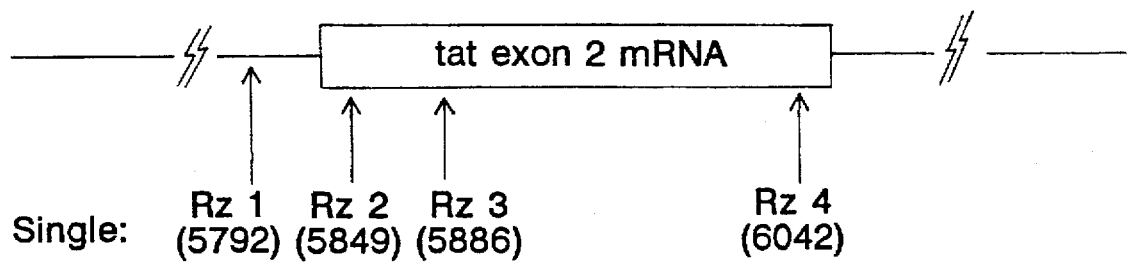

FIG. 11. The anti-HIV-1 tat ribozymes were designed according to the sequence data of HIV-1 SF2 isolated from Genebank (LOCUS: HIVSF2CG) Target sites are GUC (Rz 1), GUA (Rz 2), GUC (Rz 3) and CUC (Rz 4).

DETAILED DESCRIPTION OF THE INVENTION

This invention is directed no a synthetic non-naturally occurring oligonucleotide compound which comprises nucleotides whose sequence defines a conserved catalytic region and nucleotides whose sequence is capable of hybridizing with a predetermined target sequence within a packaging sequence of an RNA virus. Preferably, the viral packaging sequence of is a retrovirus packaging sequence and in one embodiment the HIV-1 Psi packaging sequence. The RNA virus may be HIV-1, Feline Leukemia Virus, Feline Immunodeficiency Virus or one of the viruses listed in Table I. The conserved catalytic region may be derived from a hammerhead ribozyme (see Haseloff et al. U.S. Pat. No. 5,245,678; Rossi et al. U.S. Pat. No. 5,249,796), a hairpin ribozyme (see Hampel et al., European Application No. 89 117 424, filed Sep. 20, 1989), a hepatitis delta ribozyme (Goldberg et al. PCT International Application Nos. WO 91/04319 and WO 91/04324, published Apr. 4, 1991), an RNAase P ribozyme(see Altman et al., U.S. Pat. No. 5,168,053), a group I intron (see Cech et al. U.S. Pat. No. 4,987,071), or a group II intron (see Pyle, 1993).

In one embodiment the compound may have the structure: (SEQ ID NO.:1)

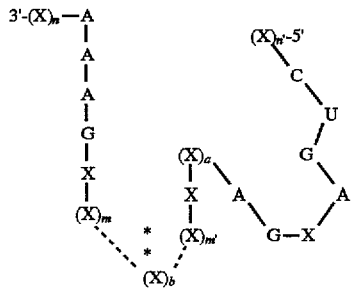

wherein each X represents a nucleotide which is the same or different and may be modified or substituted in its sugar, phosphate or base; wherein each of A, C, U, and G represents a ribonucleotide which may be unmodified or modified or substituted in its sugar, phosphate or base; wherein 3'—AAG . . . AGUCX—5' defines the conserved catalytic region; wherein each of $(X)_n$A and $(X)_n$, defines the nucleotides whose sequence is capable of hybridizing with the predetermined target sequence within the packaging sequence of the RNA virus; wherein each * represents base pairing between the nucleotides located on either side thereof; wherein each solid line represents a chemical linkage providing covalent bonds between the nucleotides located on either side thereof; wherein a represents an integer which defines a number of nucleotides with the proviso that a may be 0 or 1 and if 0, the A located 5' of $(X)_a$ is bonded to the X located 3' of $(X)_a$; wherein each of m and m' represents an integer which is greater than or equal to 1; wherein $(X)_b$ represents an oligonucleotide and b represents an integer which is greater than or equal to 2.

Alternatively, the compound may have the structure: (SEQ ID NO.:2)

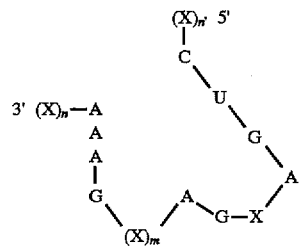

wherein 3'—AAG . . . AGUCX—5' defines the conserved catalytic region; wherein m represents an integer from 2 to 20; and wherein none of the nucleotides $(X)_m$ are Watson-Crick base paired to any other nucleotide within the compound.

In another embodiment, the compound of claim 1 having the structure: (SEQ ID NO.:3)

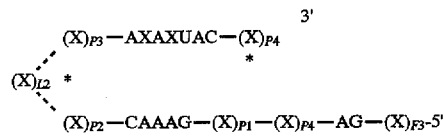

wherein 3'$(X)_{P4}$ . . . $(X)_{P1}$—5' defines the conserved catalytic region; wherein each of $(X)_{F4}$ and $(X)_{F3}$ defines the nucleotides whose sequence is capable of hybridizing with the predetermined target sequence within the packaging sequence of an RNA virus; wherein each solid line represents a chemical linkage providing covalent bonds between the nucleotides located on either side thereof; wherein F3 represents an integer which defines the number of nucleotides in the oligonucleotide with the proviso that F3 is greater than or equal to 3; wherein F4 represents an integer which defines the number of nucleotides in the oligonucleotide with the proviso that F4 is from 3 to 5; wherein each of $(X)_{P1}$ and $(X)_{P4}$ represents an oligonucleotide having a predetermined sequence such that $(X)_{P4}$ base-pairs with 3–6 bases of $(X)_{P1}$; wherein P1 represents an integer which defines the number of nucleotides in the oligonucleotide with the proviso that P1 is from 3 to 6 and the sum of P1 and F4 equals 9; wherein each of $(X)_{P2}$ and $(X)_{P3}$ represents an oligonucleotide having a predetermined sequence such that $(X)_{P2}$ base-pairs with at least 3 bases of $(X)_{P3}$; wherein each of the dashed lines independently represents either a chemical linkage providing covalent bonds between the nucleotides located on either side thereof or the absence of any such chemical linkage; and wherein $(X)_{L2}$ represents an oligonucleotide which may be present or absent with the proviso that L2 represents an integer which is greater than or equal to 3 if $(X)_{L2}$ is present.

In another embodiment, the nucleotides whose sequences define a conserved catalytic region are from the hepatitis delta virus conserved region. Alternately, the nucleotides whose sequences define a conserved catalytic region contain the sequence NCCA at its 3' terminus.

The invention is also directed to multiple compounds or ribozymes with conserved catalytic regions which may be the same or different targeted to predetermined target sequences which may be the same or different. In this embodiment, a synthetic non-naturally occurring oligonucleotide compound which comprises two or more domains which may be the same or different wherein each domain comprises nucleotides whose sequence defines a conserved catalytic region and nucleotides whose sequence is capable of hybridizing with a predetermined target sequence within a packaging sequence of an RNA virus. The compounds may also be covalently to an antisense nucleic acid compound capable of hybridizing with a predetermined sequence, which may be the same as or different from the oligonucleotide compound, within a packaging sequence of the RNA virus.

In one preferred embodiment, the nucleotides are capable of hybridizing with the 243, 274, 366 or 553 target sequence in the MoMLV and site 749 in the HIV Psi packaging site. The oligonucleotide compounds may further comprise at least one additional synthetic non-naturally occurring oligonucleotide compound or antisense molecule covalently linked, targeted to a different gene of the RNA virus genome. In the case where the RNA virus is HIV and the different region of the HIV genome may be selected from the group consisting of long terminal repeat, 5' untranslated region, splice donor-acceptor sites, primer binding sites, 3' untranslated region, gag, pol, protease, integrase, env, tat, rev, nef, vif, vpr, vpu, vpx, or tev region.

Preferably, the first oligonucleotide compound is capable of hybridizing with the 243, 274, 366 or 553 target sites or combination thereof in the MoMLV and site 749 (see Example 5) in the HIV Psi packaging site and the nucleotides of the second additional compound are capable of hybridizing with the 5792, 5849, 5886, or 6042 target sites or combination thereof in the HIV tat region. Additional targets may be found within the HIV genome (Table III), particularly within the tat sequence and within the psi packaging region (HIV-1 SF2) 636 GUGGC GCCCG AACAG GGACG CGAAA GCGAA A<u>GU</u>AGAACCA GAGGA G<u>CUCU CUC</u>GA CGCAG GA<u>CUC</u> GGC<u>UU</u> GCUGA AGCGC GCACA GCAAG AGGCG AGGGG CGGCG ACUGG UGA<u>GU</u> ACGCC AA<u>UUU UU</u>GA <u>C</u>UAGCG GAGG<u>C U</u>AGAA GGAGA GAGAG AUGGG UGCGA GAGCG 805, or Table III. The specific ribozyme sequences used here are Rz-2, Rz-M and Rz-ψ. The Anti-HIV Ribozyme Sequences Rz-2 (single anti-tat) TTAG-GAT<u>CCTGATGAGTCCGT</u>GAGGACGAAACTGGCTC Rz-M (multiple anti-tat) CCTAGGCT<u>CTGATGAGTCCGT</u>GAGGACGAAACTTCCTGTTAGG-AT<u>CCTGATGAGTCCGT</u>GAGGACGAAACTGGCTCG-C TATGTT<u>CTGATGAGTCCGT</u>GAGGACGAAACA-CCCAA Rz-ψ (single anti-HIVψ) GTCAAAAATTGGCG <u>CTGATGAGTCCGT</u>GAGGACGAAACTCACCAGTCG-CCG.

The cleavage of HIV RNA by ribozymes is a potentially useful approach. Therapeutically, it has several important properties
i) specificity,
ii) the ability to target a relatively large number of potential sites,
iii) lack of toxicity to cells,
iv) turnover of the ribozyme molecule,
v) variety of applicable delivery methods and vi) potential for a variety of methods of production: a) chemical synthesis (as in is a short molecule), b) biochemical production by in vitro transcription and c) promoter driven in vivo production from integrated constructs.

The present invention utilizes anti-packaging site (Psi) ribozymes to inhibit HIV replication. This activity would act at levels A, E, F and G. Cutting at this site can have inhibitory effects on: i) the entry of the virus into target cells ii) production of viral RNA iii) the translation of viral mRNA into viral proteins and iv) the packaging of viral genomic RNA into virions.

PSI PACKAGING SEQUENCE

The Psi packaging sequence is a cis-acting viral genomic sequence which is necessary for the specific encapsidation of viral RNA into virions (Aronoff et al., 1991). It has been shown that packaging of RNA into virus particles exhibits high specificity and this appears to be imparted by the Psi site. The location of the Psi packaging site for both Mo-MLV and HIV-1 was identified by functional deletion, that is removing certain sequences and observing whether the process of packaging of viral RNA continued. The sequence has been shown to be within the 5' untranslated region of the retrovirus and to be absent in RNAs which are not packaged. In terms of the present invention, we have deduced that, in order for the RNA to be easily recognized as one to be packaged, the packaging sequence must be exposed, accessible and able to be recognized. Studies of both the Mo-MLV and the HIV-1 packaging signal have indicated that in each case there is a conserved stable secondary structure (Alford et al., 1992 and Harrison et al., 1992). In our view these features have made the Psi packaging site an attractive target for ribozyme action. A study using antisense to the retroviral packaging sequence has previously shown that the replication of Moloney murine leukemia virus (Mo-MLV) can be inhibited in transgenic animals by interference with the Psi sequence (Han et al., 1991).

MOLONEY MURINE LEUKEMIA VIRUS (Mo-MLV) AND HUMAN IMMUNODEFICIENCY VIRUS (HIV-1)

Figure 1:
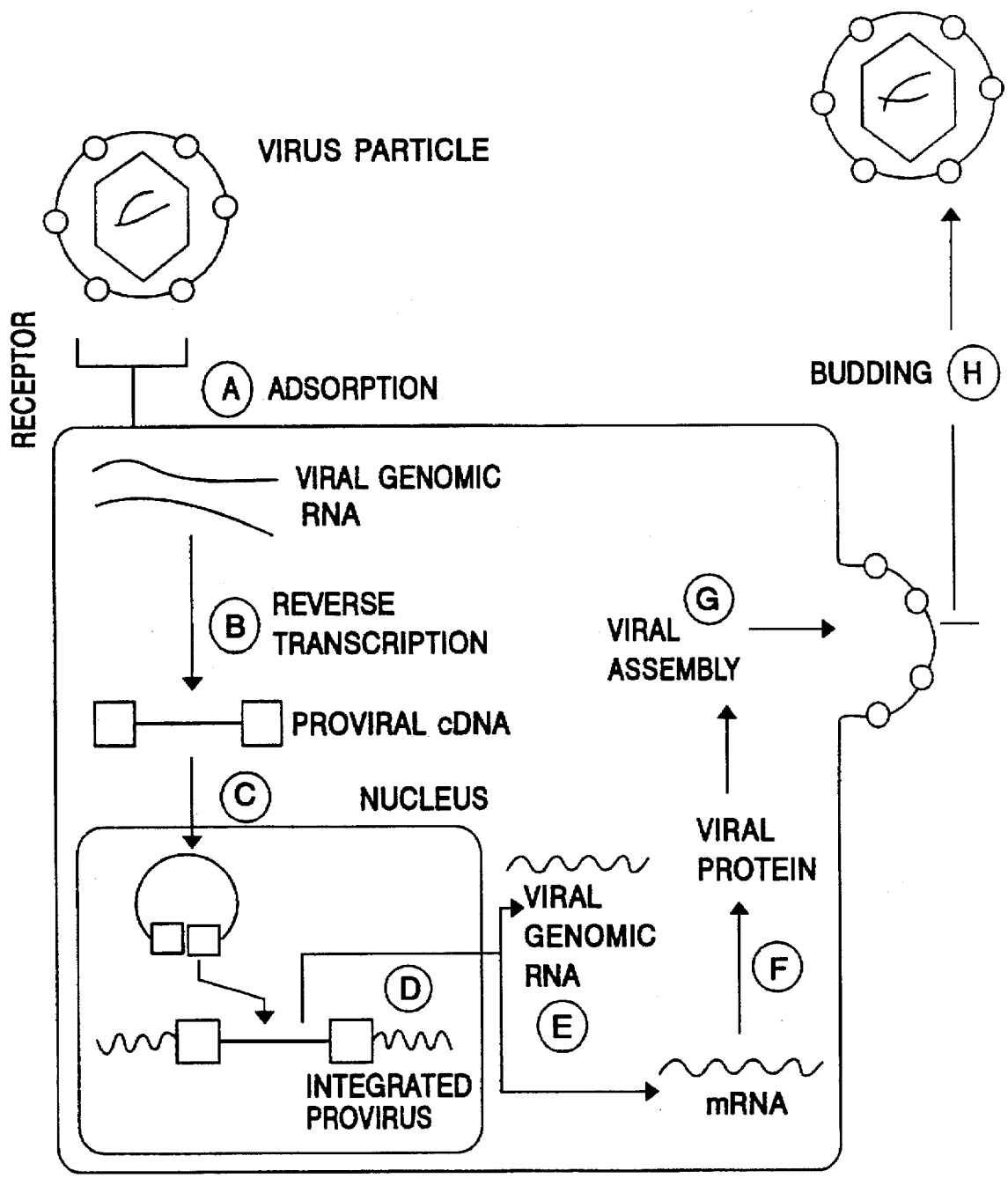
FIG. 1. Replication cycle of a typical retrovirus.
(A) Virus binds to cell surface receptors on the target cell and the genomic RNA enters the target cell following fusion and viral uncoating.
(B) Reverse transcription occurs resulting in the conversion of vital RNA into cDNA.
(C) cDNA enters the nucleus and is converted into a circular form.
(D) The cDNA then becomes integrated into the host cell genome.
(E) Transcription of the provirus to produce viral RNA and mRNA.
(F) Translation produces viral proteins.
(G) The viral core is formed from the virally encoded proteins and viral RNA packaged.
(H) The core obtains a membrane and exits the cell by budding through the cell membrane.

Mo-MLV is a murine wild type retrovirus that does not carry an oncogene (FIG. 3) (Teich et al., 1985). It causes leukemia in mice with a long latency due to insertional mutagenesis. We have used Mo-MLV as a first step for assessing proof of principle for efficacy of anti-viral ribozymes. Mo-MLV is typical retrovirus in which replication proceeds along the lines outlined in FIG. 1 and packaging is effected via the Psi packaging site. In one embodiment of the present invention, anti-Mo-MLV ribozymes targeted to the Psi packaging site and cloned within an expression vector were tested for their ability to reduce virus production in tissue culture.

HIV-1, the active principle in Acquired Immune Deficiency Syndrome (AIDS) induces cell death in T lymphocytes (McCune, 1991; Levy, 1993). These cells are vital contributors to the immune response. In any potential anti-HIV approach it is essential to substantially reduce or inhibit viral replication before the immune system becomes crippled due to loss of these cells. There is currently no effective cure for AIDS. However, by reducing viral titer it is expected that progression of the disease will be slowed and may even be arrested. Development of anti-HIV-packaging sequence ribozymes appears to be a viable method for substantially inhibiting or even halting virus production.

Anti HIV-gag ribozymes have previously been developed which were shown to be able to reduce gag-RNA and p24 levels in cells expressing the ribozyme (Sarver et al., 1990).

Hammerhead ribozymes have been developed to cleave HIV-1 integrase RNA in E. coli to block translation of the integrase protein (Sioud et al., 1991). Studies have also shown that a ribozyme that also cleaves HIV-1 RNA in the U5 region can protect T cells from HIV-1 (Dropulic et al., 1992, Ojwang et al., 1992, Lo et al., 1992, and Weerasinghe et al., 1991).

In another preferred embodiment of the present invention, anti-HIV ribozymes targeted to the Psi packaging site and cloned within the same expression vector as for the anti-Mo-MLV construct. These constructs were also tested for their abilities to reduce virus production in tissue culture.

DELIVERY OF EXPRESSION CONSTRUCTS

The major means by which to introduce the expression constructs into target cells are transfection including electroporation, liposome mediated and retrovirally mediated gene transfer.

Definitions

As used herein, "Psi packaging site" refers to a region directly proximal to the 5' LTR which is involved in encapsidation of the viral RNA into virions.

As used herein, "complementary arms" are the sequences attached to the core hammerhead ribozyme which allow binding to a specific region of the target RNA.

As used herein, "ribozyme" may be of a hammerhead hairpin, hepatitis delta, RNase P, group I intron or group II intron, which are capable of cleaving target RNA. The hammerhead ribozyme is the subject of publication of Haseloff and Gerlach (Haseloff et al., 1988) and subsequent papers by a number of laboratories.

Description

This invention relates to the treatment of viral diseases, especially AIDS, in which the pathogenic agent has RNA as its genomic material and this RNA is packaged into virions. The approach is to inhibit replication of the virus by destroying the viral RNA at the Psi packaging site, the recognition sequence necessary for packaging of the viral genomic RNA. Cutting at this site has inhibitory effects on: i) the entry of the virus into target cells and, following integration of the provirus into the host genome, ii) production of viral RNA, iii) the translation of viral mRNA into viral proteins and iv) the packaging of viral genomic RNA into virions.

In one embodiment of the invention, certain expression constructs are provided, which comprise nucleotide sequences of interest. In a preferred expression construct, a ribozyme expression construct is provided which, when introduced into a cell, which may be a Mo-MLV or HIV-1 infected cell, is capable of directing transcription of RNA which, due to complementary arms surrounding the ribozyme, can bind to Mo-MLV or HIV-1 RNA. These complementary arms are short and it is the presence of ribozyme sequences which act to cut the RNA, thereby interfering with the action of the RNA molecule.

The invention has been tested in several ways. One set of experiments showed a direct correlation between ribozyme-mediated cleavage of the Mo-MLV viral Psi packaging sequence in vitro and the in vivo suppression of Mo-MLV replication. There were three main steps which were followed in order to reach this conclusion—i) Demonstration of ribozyme-mediated in vitro clevage. ii) Transfection of constructs containing the ribozymes into Mo-MLV infected cells. iii) Various assays to show a) integration of constructs, b) ribozyme construct expression, c) effect of ribozyme construct expression on levels of virus replication.

For HIV, similar steps were followed—i) design and construction of ribozyme constructs, ii) transfection of ribozyme containing constructs into a human T lymphocyte cell line, iii) various assays to show a) integration of constructs, b) ribozyme construct expression c) effect of ribozyme construct expression on levels of virus replication.

The invention acts as a viral suppressant both to i) inhibit viral entry into a non-infected cell, by clipping the viral RNA as it enters the target cell and ii) to decrease levels of functional virus exiting the infected cell. In both cases, it acts to cut the viral RNA—at the entry point in the first case and at the exit point in the second. In the latter case, cutting decreases RNA levels by cutting both viral and mRNA. Cutting specifically at the Psi packaging site also serves to inhibit packaging of the viral RNA.

Several considerations were employed in order to choose a target for anti-viral ribozyme action. The criteria used for the present invention were—i) The target must be functionally important. ii) There must be a high degree of sequence conservation among the different HIV-1 isolates in the target region. iii) In the case of hammerhead ribozymes, the ribozyme target sequence such as GUC or GUA is preferably present in the sequence or the related triplets GUU, CUC etc. (Perriman, et al., 1992) iv) The target sequence should be readily accessible, for example it should lack extensive secondary structure (Rossi et al., 1992).

The Psi packaging site fitted the above criteria and was chosen as a target for cleavage by ribozymes. This site has: i) an essential function in the retroviral replication cycle, ii) relative accessibility, being a site on the RNA that must be recognized and accessible to other components in order for packaging to occur and iii) a conserved nature among different strains of the same virus.

It has been observed that in different strains of both Mo-MLV and HIV there is strong conservation of sequence and structure in the Psi packaging region of each virus. While there is no apparent conservation of structure or sequence between the packaging site of HIV and Mo-MLV, due to the identical function of the Psi site in each virus, it is reasonable to assume there must be similarities. The secondary structure of viral RNA was examined and sites on the Psi sequence were chosen that appeared to be accessible to ribozyme action. These were in the loop regions, that is single-stranded unpaired base regions of the RNA. Zuker's FOLDRNA program was used to locate non-base paired regions of the Psi packaging sequence. The ribozymes were designed to target these sites. The sites chosen also had a GUC base sequence present.

Figure 4:
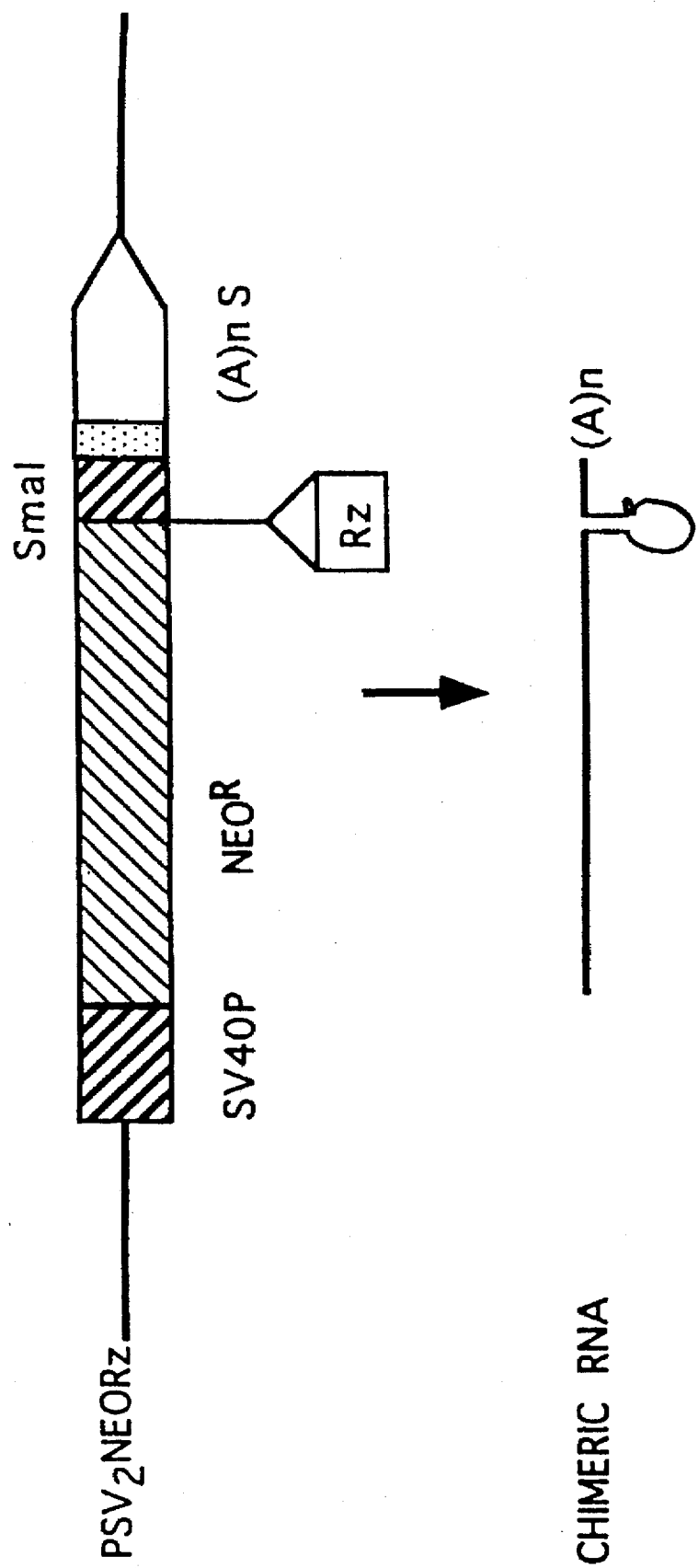
FIG. 4. Anti-Mo-MLV and Anti-HIV packaging site constructs.

The constructs used in the present invention employed ribozymes inserted into the 3' untranslated region of neomycin resistance gene (neo$^r$). The basic construct is shown in FIG. 4. Such a construct allowed assessment of integration and expression. The former being determined by Southern analysis, the latter by cellular resistance to G418 toxicity and by RNAse protection assay. A further advantage of the design employed was that the chimeric RNA with a small ribozyme sequence in the 3' end of a larger neo$^r$ gene messenger appeared to act to keep the ribozymes stable within the cells. The latter is an extremely important point as without stability the effect of ribozymes will be minimal.

DISCUSSION

The invention provides the basis for a process by which ribozymes could be used to protect animals, including humans, from diseases caused by retroviruses. The basic principle of the invention is to incorporate, within a larger gene, ribozymes against the packaging site of the target retrovirus. The carrier gene may either be selectable (as in the present case) or non-selectable. Expression of the larger carrier gene provides a more stable chimeric ribozyme RNA molecule. The DNA construct is transfected into either a naive cell population to protect the cells or can be introduced into a virally-infected cell population to reduce viral titre. In a further embodiment, the ribozyme expression construct can also be introduced by retrovirally mediated gene transfer to increase the efficiency of introduction. A third embodiment of this invention is a retrovirus which carries an anti-packaging site ribozyme. If the retroviral vector is an MoMLV based, then the ribozyme targeted to the packaging site of HIV will not cleave the MoMLV packaging site due to sequence divergence for the two retroviruses Therapeutically, the application could involve introduction to the constructs into T lymphocytes ex vivo or into hematopoietic stem cells ex vivo. One preferred approach would be to incorporate the ribozyme constructs into lymphocytes or stem cells via a retroviral vector such as amphotropic Mo-MLV. Hematopoietic progenitor and true stem cells are promising targets for gene therapy because they are present in the bone marrow or can be mobilized into the peripheral blood. Progenitor cells may give rise to both myeloid and lymphoid cells, true stem cells giving rise to cells of all cellular lineages. Therapy could involve irradiation to destroy the HIV infected hematopoietic system and the stem cells containing the ribozyme would then be injected into the patient. As a result the patient's cells could be rendered resistant to HIV.

The invention is also directed to transfer vectors comprised of RNA or DNA or a combination thereof containing a nucleotide sequence which on transcription gives rise to the compounds described above. The transfer vector may be the HIV long terminal repeat, an adenovirus associated transfer vector, an SV40 promoter, Mo-MLV, or an amphotropic retrovirus vector. The transfer vector may further comprise a sequence directing the oligonucleotide compound to a particular organ or cell in vivo or a particular region within the cell. Examples of localizing to a particular region of a cell include the use of the packaging signal (Sullenger et al. 1993). The invention is also directed to compositions containing the compounds or transfer vectors described above in a suitable carrier. The carrier may be a pharmaceutically, veterinarially, or agriculturally acceptable carrier or excipient. The composition may further comprise a TAR decoy, polyTAR or a RRE decoy.

For production of the DNA sequences of the present invention in prokaryotic or eukaryotic hosts, the promoter sequences of the present invention may be either prokaryotic, eukaryotic or viral. Suitable promoters are inducible, repressible, or, more preferably, constitutive. Examples of suitable prokaryotic promoters include promoters capable of recognizing the T4 polymerases (Malik, S. et al., *J. Molec. Biol.* 195:471–480 (1987) Hu, M. et al., *Gene* 42:21–30 (1986), T3, Sp6, and T7 (Chamberlin, M. et al., Nature 228:227–231 (1970); Bailey, J. N. et al., *Proc. Natl. Acad. Sci. (U.S.A.)* 80:2814–2818 (1983); Davanloo, P. et al., *Proc. Natl. Acad. Sci. (U.S.A.)* 81:2035–2039 (1984)); the $P_R$ and $P_L$ promoters of bacteriophage lambda (*The Bacteriophage Lambda*, Hershey, A. D., Ed., Cold Spring Harbor Press, Cold Spring Harbor, N.Y. (1973); *Lambda II*, Hendrix, R. W., Ed., Cold Spring Harbor Press, Cold Spring Harbor, N.Y. (1980)); the crp recA, heat shock, and lacZ promoters of *E. coli*.; the int promoter of bacteriophage lambda; the bla promoter of the β-lactamase gene of pBR322, and the CAT promoter of the chloramphenicol acetyl transferase gene of pPR325, etc. Prokaryotic promoters are reviewed by Glick, B. R., (*J. Ind. Microbiol.* 1:277–282 (1987)); Cenatiempo, Y. (*Biochimie* 68:505–516 (1986)); Watson, J. D. et al. *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981) and the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)).

For preparation of vectors for use in inhibiting retrovirus infection, in susceptible eukaryotic cells or in whole animals, eukaryotic promoters must be utilized, as described above. Preferred promoters and additional regulatory elements, such as polyadenylation signals, are those which should yield maximum expression in the cell type which the retrovirus to be inhibited infects. Thus, for example, HIV-1, HIV-2, HTLV-1 and HTLV-2, as well as the Moloney murine leukemia virus, all infect lymphoid cells, and in order to efficiently express a ribozyme construct alone or in combination with an antisense RNA complementary to the packaging sequence of one (or more) of these viruses, a transcriptional control unit (promoter and polyadenylation signal) are selected which provide efficient expression in hematopoietic, particularly lymphoid cells (or tissues). As exemplified below, preferred promoters are the cytomegalovirus immediate early promoter (32), optionally used in conjunction with the growth hormone polyadenylation signals (33), and the promoter of the Moloney-MuLV LTR, for use with a lymphotropic retrovirus. A desirable feature of the Moloney-MuLV LTR promoter is that it has the same tissue tropism as does the retrovirus. The CMV promoter is expressed in lymphocytes. Other promoters include VA1 and tRNA promoters. The metallothionein promoter has the advantage of inducibility. The SV40 early promoter exhibits high level expression in vitro in bone marrow cells.

The invention is also directed to methods for producing the compounds which comprise the steps of: (a) ligating into a transfer vector comprised of DNA, RNA or a combination thereof a nucleotide sequence corresponding to the compound; (b) transcribing the nucleotide sequence of step (a) with an RNA polymerase; and (c) recovering the compound.

The invention is also directed to prokaryotic or eukaryotic host cells comprising a nucleotide sequence which is, or on transcription gives rise to the compounds described above. The cell may be an animal cell, a hematopoietic stem cell which gives rise to progenitor cells, more mature, and fully mature cells of all the hematopoietic cell lineages, a progenitor cell which gives rise to mature cells of all the hematopoietic cell lineages, a committed progenitor cell which gives rise to a specific hematopoietic lineage, a T lymphocyte progenitor cell, an immature T lymphocyte, a mature T lymphocyte, a myeloid progenitor cell, or a monocyte/macrophage cell.

The invention is also directed to the use of the compounds above to protect hematopoietic stem cells, progenitor cells, committed progenitor cells, T lymphocyte progenitor cells, immature T lymphocytes, mature T lymphocytes, myeloid progenitor cells, or monocyte/macrophage cells. Further, method to suppress/treat or protect against HIV in a patient which comprises the introduction of the transfer vector above into hematopoietic cells thereby rendering the cells resistant to HIV so as to thereby suppress/treat or protect against HIV. The introduction is ex vivo and the cells are autologous or heterologous cells with or without myeloablation. In one embodiment of the present invention, three single and one multiple hammerhead ribozymes were designed to target different sites within the Mo-MLV Psi packaging site and one ribozyme was designed to target a site within the HIV Psi packaging site (See FIG. 2). Mo-MLV was chosen as an example of a retrovirus in which to determine principles of action. These principles would apply to other retroviruses including HIV. Testing was also carried out for HIV-1.

In the present invention the nonhuman animal and progeny thereof contain at least some cells that express or retain the non-naturally occuring oligonucleotide compound. The transgenic nonhuman animal all of whose germ and somatic cells contain the non-naturally occuring oligonucleotide compound in expressible form introduced into said animal, or an ancestor thereof, at an embryonic stage as described in U.S. Pat. Nos. 4,736,866, 5,175,383, 5,175,384, or 5,175,385. See also (Van Brunt, 1988; Hammer, 1985; Gordon et al., 1987; Pittius et al., 1988; Simons et al. 1987; Simons et al., 1988).

The invention also includes a process for rendering cells resistant to viral infection which comprises treating the cells with the non-naturally occuring oligonucleotide compound described above. Preferably, the treatment is ex vivo. In addition as used herein the terms antisense and ribozymes also include compounds with modified nucleotides, deoxynucleotides, peptide nucleic acids, etc. These would be used for ex vivo treatment or topical treatment.

An effective amount of the non-naturally occuring oligonucleotide compound of the present invention would generally comprise from about 1 nM to about 1 mM concentration in a dosage form, such as a cream for topical application, a sterile injectable composition, or other composition for parenteral administration. In respect of topical formulations, it is generally preferred that between about 50 µM to about 500 µM non-naturally occuring oligonucleotide compound be employed. Compounds comprising nucleotide derivatives, which derivatives may involve chemically modified groups, such as phosphorothioate or methyl phosphonate derivatives may be active in nanomolar concentrations. Such concentrations may also be employed to avoid toxicity.

Therapeutic strategies involving treatment of disease employing compounds of this invention are generally the same as those involved with antisense approaches, such as described in the anti-sense bibliography of (Chrisley, 1991). Particularly, concentrations of compounds utilized, methods and modes of administration, and formulations involved may be the same as those employed for antisense applications.

An "effective amount" as used herein refers to that amount which provides a desired effect in a mammal having a given condition and administration regimen. Compositions comprising effective amounts together with suitable diluents, preservatives, solubilizers, emulsifiers, adjuvants and/or carriers useful for therapy. Such compositions are liquids or lyophilized or otherwise dried formulations and include diluents of various buffer content (e.g., Tris-HCL, acetate phosphate), pH and ionic strength, additives such as albumin or gelatin to prevent absorption to surfaces, detergents (e.g., Tween 20, Tween 80, Pluronic F68, bile acid salts), solubilizing agents (e.g., Thimerosal, benzyl alcohol), bulking substances or tonicity modifiers (e.g., lactose, mannitol), covalent attachment of polymers such as polyethylene glycol to the non-naturally occuring oligonucleotide compound, complexation with metal ions, or incorporation of the material into or onto particulate preparations of polymeric compounds such as polylactic acid, polyglycolic acid, polyvinyl pyrrolidone, etc. or into liposomes, microemulsions, micelies, unilamellar or multilamellar vesicles, erythrocyte ghosts, or spheroplasts. Such compositions will influence the physical state, solubility, stability, rate of in vivo release, and rate of in vivo clearance of the oligonucleotide. Other ingredients optionallymay be added such as antioxidants, e.g., ascorbic acid; low molecular weight (less than about ten residues) polypeptides, i.e., polyarginine or tripeprides; proteins, such as serum albumin, gelatin, or immunoglobulins; amino acids; such as glycine, glutamine acid, aspartic acid, or arginine; chelating agents such as EDTA; and sugar alcohols such as mannitol or sorbitol. Possible sustained release compositions include formulation of lipophilic depots (e.g., fatty acids, waxes, oils). Also comprehended by the invention are particulate compositions coated with polymers (e.g., polyoxamers or polyoxamines) and non-naturally occuring oligonucleotide compound coupled to antibodies directed against tissue-specific receptors, ligands or antigens or coupled to ligands of tissue-specific receptors. Further, specific nucleotide sequences may be added to target the non-naturally occuring oligonucleotide compound of this invention to the nucleus, plastid, cytoplasm or to specific types of cells. Other embodiments of the compositions of the invention incorporate particulate forms protective coatings, protease inhibitors or permeation enhancers for various routes of administration, including parenteral, pulmonary, nasal and oral.

Suitable topical formulations include gels, creams, solutions, emulsions, carbohydrate polymers, biodegradable matrices thereof; vapors, mists, aerosols, or other inhalants. The non-naturally occuring oligonucleotide compound my be encapsulated in a wafer, wax, film or solid carrier, including chewing gums. Permeation enhancers to aid in transport to movement across the epithelial layer are also known in the art and include, but are not limited to, dimethyl sulfoxide and glycols.

Ribonucleotide and deoxyribonucleotide derivatives or modifications are well known in the art, and are compatible with commercially available DNA synthesizers. (See Saenger, 1984, particularly pages 159–200). Nucleotides comprise a base, sugar and a monophosphate group. Accordingly, nucleotide derivatives, substitutions, or modifications may be made at the level of the base, sugar, or monophosphate.

A large number of modified bases are found in nature, and a wide range of modified bases have been synthetically produced (Saenger, 1984; and CRC Handbook of Biochemistry). Suitable bases would include inosine, 5'-methylcytosine, 5'-bromouracil, xanthine, hypoxanthine and other such bases.

For example, amino groups and ring nitrogens may be alkylated, such as alkylation of ring nitrogen atoms or carbon atoms such as $N^1$ and $N^7$ of guanine and $C^5$ of cytosine; substitution of keto by thioketo groups; saturation of carbon=carbon double bonds, and introduction of a C-glycosyl link in pseudouridine. Examples of thioketo derivatives are 6-mercaptopurine and 6-mercaptoguanine.

Bases may be substituted with various groups, such as halogen, hydroxy, amine, alkyl, azido, nitro, phenyl and the like. Bases may be substituted with other chemical species, such as an amino-acid side chain or linkers which may or may not incorporate other chemical entities, e.g. acidic or basic groups. For example, guanine ($G_3$) may be substituted with tyrosine, and cytosine (C1) or adenine (A11) similarly substituted with histidine.

The sugar moiety of the nucleotide msy also be modified according to well known methods in the art (Saenger, 1984). This invention embraces various modifications to the sugar moiety of nucleotides as long as such modifications do not abolish cleavage activity of the compound. Examples of modified sugars include replacement of secondary hydroxyl groups with halogen, amino or azido groups; 2'-methylation;

conformational variants such as the O$_2$'-hydroxyl being cis-oriented to the glycosyl C$_1$, —N link to provide arabinonucleosides, and conformational isomers at carbon C$_1$, to give α-nucleosides, and the like. Further, non ribose sugars may be used such as hexoses such as glucose, pentoses such as arabinose.

The phosphate moiety of nucleosides is also subject to derivatisation or modifications, which are well known in the art. For example, replacement of oxygen with nitrogen, sulphur or carbon derivatives to respectively give phosphoramidates, phosphorothioates, phosphodithiolates, and phosphonates. Substitutions of oxygen with nitrogen, sulphur of carbon derivatives may be made in bridging or non bridging positions. It has been well established from work involving antisense oligonucleotides that phosphodiester and phosphorothioate derivatives may efficiently enter cells (particularly when of short length), possibly due to association with a cellular receptor. Methylphosphonates are probably readily taken up by cells by virtue of their electrical neutrality.

The phosphate moiety may be completely replaced with peptide nucleic acids (see Hanvey et al., 1992; Nielson, 1991; and Egholm, 1992). Other replacements are well-known to those skilled in the art for example siloxane bridges, carbonate bridges, acetamidate bridges, carbamate bridges, thioether bridges, etc. (Uhlmann and peymann, 1990).

The following examples are for illustration of the claimed invention. This invention is illustrated in the Experimental Detail sections which follow. These sections are set forth to aid in an understanding of the invention but are not intended to, and should not be construed to, limit in any way the invention as set forth in the claims which follow thereafter.

EXAMPLE 1

In vitro Ribozyme-Catalyzed Cleavage of Mo-MLV Psi Packaging Sequences.

In order to show that the target sites were indeed cleavable, in vitro cleavage reactions were performed prior to ribozyme testing in cell culture.

Figure 2:
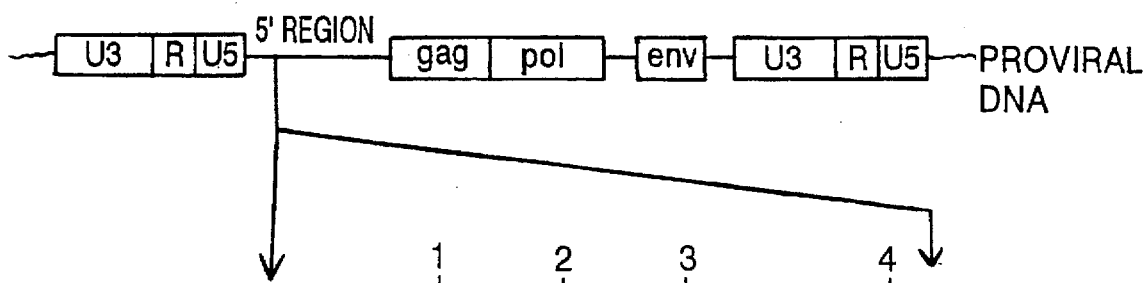
FIG. 2. Ribozyme targeting sites within the Mo-MLV Psi packaging region. Mo-MLV 5' region represents a BalI/BalI fragment (nt 212 to nt 747) of pMLV-1 (defined in the text). Arrows indicate the ribozyme targeting sites all of which were GUC residues.

Four sites were chosen in the Mo-MLV packaging region according to the presence of GUC bases and the potential accessibility of the sites within the proposed RNA secondary structure derived from Zuker's FOLDRNA program (Zuker et al., 1981). The sites were designated 243, 274, 366 and 553, based on their nucleotide distance from the 5' end of the viral transcript (FIG. 2). These nucleotide positions are as described in RNA Tumor Viruses (Coffin, 1985). Two types of ribozyme were designed: three single ribozymes targeted individually to sites 243, 274 and 366 with arms of length 12 nucleotides and one multiple ribozyme targeted to all four sites with intervening arms of the length of sequences between each of the target sites. The sites and overall design are shown in FIG. 2.

The single ribozymes were constructed by cloning an artificial double stranded insert with overhanging PstI and EcoRI ends into pGEM3Zf(+). The resulting plasmids were pGEM243, pGEM274 and pGEM366. The multiple ribozyme was constructed by a variation of standard in vitro mutagenesis protocols (Warrilow et al., 1992). This plasmid was termed pGEM-M7. Successful cloning and sequence integrity were confirmed by DNA sequencing.

The Psi packaging sequence, in the Bal I-Bal I fragment of Mo-MLV derived from pMLV-1 (Coffin, 1985), was cloned into the pGEM3Zf(+) vector and transcribed as a substrate for in vitro ribozyme cleavage. Run-off transcription mixture (50 μl) for generating either ribozymes or substrate contained 1 μg linearized proteinase K treated DNA template, 30 mM dithiothreitol, 400 uM of each rNTPs, 40mM Tris-Cl, pH 8.0, 2 mM spermidine, 6 mM MgCl$_2$, 50 mM NaCl, 1 μl of [$\alpha$-$^{32}$P]-UTP (400–800 Ci/mmole, 10 mCi/ml), 1 unit RNasin and 10 units T7 or SP6 RNA polymerase (Stratagene). After 1 h incubation at 37° C., 10 units of RNase-free DNase (Promega) were added, and the mixture was incubated for 15 min at 37° C. After phenol-chloroform extraction, RNA transcripts were precipitated by adding 0.1 volume of 3M sodium acetate and 2.5 volume of ethanol. For cleavage reactions, the ribozyme and substrate (1:1 molar ratio) were pre-incubated at 80° C. for 2 minutes, followed by 30 minutes of incubation at 37° C. in the presence of 50 mM Tris-Cl, pH 7.5 and 10 mM MgCl$_2$. Reactions were stopped by the addition of an equal volume of stop mix (8M urea, 50 mM EDTA, 0.05% bromphenol blue and 0.05% xylene cyanol) and analyzed on a denaturing 6% polyacrylamide gel containing 8M urea, followed by autoradiography.

Engineered ribozymes targeted to different sites of the Mo-MLV proviral packaging sequence were shown to cleave target RNA in vitro at the chosen sites.

Figure 3:
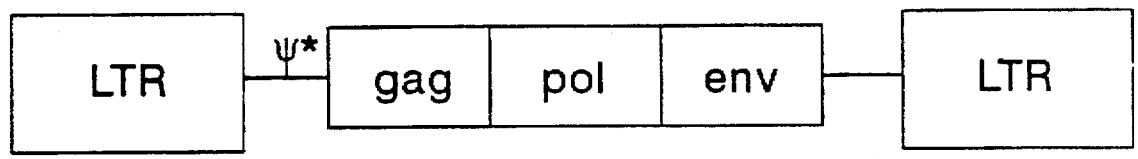
FIG. 3. Genome of Moloney murine leukemia virus The genome of MoMLV consists of the replicarive genes gag, pol and env and the 5' and 3' long terminal repeats (LTRs). The Psi packaging site is necessary for packaging of the viral ENA into the virion.

For the majority of the ribozyme constructs, incubation of a $^{32}$P-labelled Psi transcript with $^{32}$P-labelled ribozyme RNA in an approximately equimolar amount led to efficient cleavage of the substrate under mild physical conditions (37° C., 10 mM MgCl$_2$ and 50 mM Tris.Cl, pH 7.5). Representative examples of these digestions are shown in FIG. 6. The size of the cleaved Psi fragments produced by Rz274 and Rz366 were consistent with the location of predicted sites for cleavage, resulting in bands of 62nt plus 473nt and 154nt plus 381nt respectively. The multiple ribozyme (Rz-M7) produced four fragments (50nt, 92nt, 187nt and 240nt) as predicted as well as several partially cleaved fragments (FIG. 3). For Rz243, there was no visible cleavage at 37° C. and weak cleavage, yielding appropriate size fragments, at 50° C. (data not shown). With the exception of ribozyme 243, these results indicated efficient site-specific ribozyme mediated cleavage.

EXAMPLE 2

Anti-Mo-MLV Packaging Site (Psi) Constructs

Following demonstration of efficient in vitro cleavage, the engineered ribozymes as well as a long antisense sequence complementary to the Psi packaging region were cloned into the 3' untranslated region of the neo$^r$ gene coupled to the simian virus 40 (SV40) early promoter (FIG. 4). neo$^r$ is a prokaryotic gene which codes for an enzyme that phosphorylates and, thereby inactivates neomycin or the neomycin analogue G418. The latter is toxic for mammalian cells and the expression of an exogenous neo$^r$ gene permits cell survival. This construct with the SV40 promoter coupled to the neo$^r$ gene is within a mammalian expression vector, pSV2neo and is shown diagrammatically in FIG. 4.

The ribozyme inserts and an antisense control were cloned into a SmaI site in the 3' untranslated region of neo$^r$ by blunt-ended ligation. The resultant vectors were termed pSV243, pSV274, pSV366, pSVM7 and pSVas Psi (the antisense construct) respectively.

EXAMPLE 3

Transfection of constructs into 3T3-Mo-MLV producing cell lines.

The various pSV2neo based constructs were transfected into 3T3-Mo-MLV cells using a calcium phosphate transfection protocol (Chen et al., 1987). Positive colonies were those that formed after 9–12 days in the presence of 500 μg/ml of G418. For each construct, 4–7 colonies were isolated using cloning cylinders. These colonies were grown, stored in liquid $N_2$ and then used for further assays. After 10–14 days selection in 500 μg/ml of G418, several stable clonal cell lines for each construct were established. To confirm the integration of transfected DNA expression constructs, genomic DNA was prepared from certain of the transfected cell lines and Southern analysis performed. The restriction enzymes HindIII and NruI were used to digest genomic DNA to generate a fragment containing the $neo^r$ gene plus inserts (ribozymes or antisense). Presence of the construct could then be determined by using a $neo^r$ specific probe. From the Southern analysis shown in FIG. 7, it is clear that the cells transfected with both ribozyme and antisense constructs and selected in G418 contain the $neo^r$ gene plus appropriate ribozyme or antisense sequences. The size of the HindIII-NruI fragments hybridizing with the $neo^r$ probe were found to be the predicted size in each case, namely 1.3 kb for $neo^r$ gene alone; 1.38 kb for $neo^r$ plus the single ribozyme; 1.98 kb for $neo^r$ plus a multiple ribozyme; 1.89 kb for $neo^r$ plus the antisense sequence.

Expression of the ribozyme or antisense constructs was predicted due to G418 resistance in the positive transfectants. This was further examined in the transfected cells using RNase protection assay. Total RNA was extracted using a guanidium thiocyanate procedure from certain of the cell lines, 20 μg of total RNA was then hybridized with the corresponding $^{32}$P-labelled riboprobes ($5 \times 10^4$ cpm) in a solution containing 80% deionized formamide, 100 mM sodium citrate pH 6.4, 300 mM sodium acetate pH 6.4, 1 mM EDTA, followed by RNase digestion of the hybridized RNAs (5 μg/ml RNase A and 10 units/ml RNaseT1). If the ribozyme was not expressed, then the complementary riboprobe would be unable to bind. The RNA would then remain single stranded and would be totally digested by RNase. The reaction mixture was then separated by electrophoresis. As shown in FIG. 8, the assays revealed that all the ribozymes and antisense constructs were expressed as expected. The protected fragments are 65 bp (single ribozymes); 588 bp multiple ribozymes and 524 bp (antisense).

EXAMPLE 4

Ability of Constructs to Suppress Mo-MLV Replication.

After the establishment of stable 3T3 Mo-MLV clonal cell lines transfected with different constructs, XC plaque assay was employed to evaluate the level of Mo-MLV replication. XC assay is a syncitial plaque assay for Mo-MLV, which is based on the observation that Mo-MLV-producing cells can cause fusion of XC cells. Mo-MLV was titrated as described in (Gautsch et al., 1976) except that 8 μg/ml polybrene (Sigma) was present during infection to enhance viral binding to the target cells. Supernatants from the culture of the different Mo-MLV-producing cell lines were added to uninfected mouse NIH3T3 cells which were pre-treated with 8 μg/ml polybrene for 1 hr prior to infection. After 20 hr incubation in growth medium, the infected NIH3T3 cells were co-cultivated with XC cells in a $2 \times 2$ mm$^2$ grided plate for 3 to 4 days. The plates were then fixed with methanol, stained with 1% methylene blue plus 0.1% Gentian violet and scanned for syncitiumplaques by microscopy. To ensure that the assays were performed within the linear portion of the dose-response curve, $3.5 \times 10^5$ cells per plate were infected with two-fold serial dilutions of the virus and passaged 24 hr later to a mixed culture with XC cells. The results in Table 1 were from three independent experiments.

74% to 77% inhibition of syncitiumplaque formation were observed from the cells containing Rz274, Rz366, Rz-M7 and As-Psi in relation to pSV2neo vector-containing cells, whereas no apparent inhibition was shown for Rz243-containing cells. These data are consistent with in vitro cleavage results (FIG. 6) in which Rz243 did not appear to efficiently cleave the substrate under the conditions used.

These suppressive effects were confirmed using viral RNA dot-blotting in which 1 ml of supernatant from a 16 hr culture of NIH3T3 virus-producing cells was clarified by centrifuging (12,000 rpm, 10 min, 4° C.) in a microcentrifuge. Viral RNA was precipitated in 8% PEG 8000 and 0.5M NaCl. After phenol-chloroform extraction, RNA was blotted onto positively charged nylon membrane (Zeta-Probe, Bio-Rad) in an alkali transfer solution (Reed et al., 1985). Hybridization was performed at 42° C. overnight in 50% formamide, 5×SSPE, 5×Denhardt's solution, 0.5% SDS, 100 mg/ml denatured herring sperm DNA and $^{32}$P-labelled riboprobe transcribed from T7 promoter of pGEM-Psi. Viral RNA was quantitated by dot scintillation counting. Viral RNA in the supernatants from the ribozyme or antisense-transfected 3T3-Mo-MLV cells was measured and compared with that in the supernatant from pSV2neo-transfected 3T3-Mo-MLV cells. As can be seen from FIG. 9 and Table 2 (except for Rz243-expressing cells), the amount of viral RNA produced from all the cell lines expressing ribozymes or antisense was substantially reduced by amounts similar to those seen by syncytia assay.

Following transfection of these ribozyme constructs into Mo-MLV infected cells, only those ribozymes which showed efficient in vitro cleavage exhibited the ability to suppress (approximately 70–80%) Mo-MLV replication in vivo. These results demonstrate a direct correlation between in vitro cleavage and in vivo ribozyme mediated virus suppression.

The previous experiments became the basis for further studies of ribozymes designed to target sites on the HIV Psi packaging sequence in order to reduce viral titre.

TABLE 1

Syncitium plaques induced by Mo-MLV released from transfected cells

| Cell* | Syncitium plaques† | Inhibition (%) |
|---|---|---|
| Rz243 | 32 ± 12 | — |
| Rz274 | 7 ± 3 | 77 |
| Rz366 | 8 ± 1 | 74 |
| Rz-M7 | 7 ± 3 | 77 |
| As-Psi | 8 ± 2 | 74 |
| pSV2neo | 31 ± 1 | 0 |

*$10^{-2}$ dilution of the supernatant from Rz or As Construct-containing cells was used in infection of NIH3T3 cells.
†The number is a mean of the plaque counts from two clonal lines of each construct in three independent experiments. The numbers are presented as the mean ± standard error. Replicate plates receiving the same dilution of infected cells generally contained similar numbers of syncitial plaques.

TABLE 2

Degree of hybridization to viral RNA dot blots

| Sample | cpm × $10^{-3}$* | Inhibition (%) |
|---|---|---|
| tRNA | 0.00 | — |
| Rz243 | 2.59 | 21 |
| Rz274 | 0.63 | 81 |
| Rz366 | 1.36 | 59 |

TABLE 2-continued

Degree of hybridization to viral RNA dot blots

| Sample | cpm × 10$^{-3}$* | Inhibition (%) |
|---|---|---|
| Rz-M7 | 0.93 | 72 |
| As-ψ | 0.96 | 71 |
| pSV2neo | 3.30 | 0 |

*cpm counts were derived from two blots in 1:1 dilution row. The viral RNA dot blot assay was carried out as described in Materials and Methods. Following autoradiography, the filters corresponding to each dot were excised for liquid scintillation counting.

EXAMPLE 5

The Anti- HIV Packaging Site Construct.

One GUA site was chosen in the HIV-1 (HIVSF2, Levy, 1984) Psi packaging region (nuc. 735 to nuc. 765 from 5' end of HIV genome) for ribozyme targeting. As for the previous constructs, the synthetic ribozyme insert was cloned into a Sma 1 site in the 3' untranslated region of the neo$^r$ gene of pSV2neo vector by blunt-ended ligation. Successful cloning and sequence integrity were confirmed by DNA sequencing. This construct was termed pSV-Rz-HIV-Psi. FIG. 4 shows a diagram of the construct.

EXAMPLE 6

Transfection of pSV-Rz-HIV-Psi construct into T lymphocytes.

The anti-HIV packaging site construct, pSV-Rz-HIV-Psi, was electroporated into Sup T-1 cells, a human T lymphoma cell line. Exponentially growing cells were harvested and the number of viable cells counted by dye exclusion. The cells were washed with PBS and resuspended at a density of 1×10$^7$ viable cells/ml in RPMI media without FCS but containing 10 mM dextrose and 0.1 mM dithiothreitol. 0.4 ml of the cell suspension and 10 μg of pSV-Rz-HIV-Psi plasmid DNA were used per electroporation in 0.4 cm cuvettes (Bio-Rad). The cell and DNA mixture was subjected to a single pulse of 960 μF, 200V from a Gene Pulser (Bio-Rad). After shocking, the cuvette was incubated for 10 minutes at room temperature, and the cells were then transferred to 10 ml of RPMI media with 10% FCS and placed into an incubator (5%CO$_2$, 37° C.). At 48 hours post electroporation, the cells were selected in medium supplemented with 800 μg/ml G418. 9–12 days later, positive colonies were isolated and grown as clonal isolates to be used in a HIV protection assay.

EXAMPLE 7

Assessment of Ability of Ribozyme Expression Constructs to Confer Protection against HIV challenge.

Two assays, p24 antigen and syncytium formation, were performed to assess efficacy of the anti-HIV Psi ribozyme construct in cell culture. HIV-1 p24 antigen assay is an enzyme immunoassay, which uses a murine monoclonal antibody against HIV core antigen coated onto microwell strips. The HIV-1 syncytiumassay is based on the observation that HIV-1 interacts with target T lymphocytes by causing fusion resulting in the formation of syncytia, large cells containing many nuclei. The clonal ribozyme-construct expressing cells, plus controls, were infected with HIV-1 (SF2) at m.o.i. of 0.1 to 1. After 2 hours, the cells were washed, and 10 ml of fresh media was added. Every 3–4 days, the number of both syncitia and viable cells were counted. For syncitia formation, approximately a two log higher dose was required in order to show the same result as in the control which did not include the ribozyme (Table 3). In addition, the presence of the ribozyme caused a delay in syncitia formation (Table 4).

In another experimental protocol, the cells were pelleted, and an aliquot of the supernatant taken for p24 assay. Representative results are shown in FIG. 10. In this experiment there was an inhibition of p24 levels to day 22 post challenge. At days 8 and 13 post-infection, more than an 80% inhibition of p24 production was observed in ribozyme-expressing cells compared to cells containing vector alone, whereas at day 22 an approximately 60% level of inhibition was observed.

These results provide evidence that HIV replication can be inhibited by the addition of a ribozyme against the Psi packaging site into T lymphocytes.

TABLE 3

Syncitia Formation

| Clones | Virus Dilution* | | | |
|---|---|---|---|---|
| | 10$^{-3}$ | 10$^{-4}$ | 10$^{-5}$ | 10$^{-6}$ |
| Rz-2 | ++++ | +— | —— | —— |
| Rz-M | ++++ | —— | —— | —— |
| Rz-Psi | ++++ | ++— | +— | —— |
| Random | ++++ | ++++ | ++— | +— |
| pSV2neo | ++++ | ++++ | ++++ | ++— |

*HIV-1 (SF33) was used in the infectivity assay (m.o.i. of 0.1–1).

TABLE 4

Syncitia formation of infected SupT1 cells

| Group | Days Post Infection | | | | | |
|---|---|---|---|---|---|---|
| | 6 | 7 | 8 | 9 | 10 | 11 |
| pSV-Rz-HIV Psi | − | − | − | − | − | − |
| pSV2neo | − | + | ++ | +++ | +++ | +++ |
| Mock | − | − | − | − | − | − |

The number of syncitia in each culture was counted in four low-power fields and was averaged, −, no syncytia; +, 1–5 syncytia; ++, 6–10 syncytia; +++, greater than 10 syncytia. Mock is uninfected SupT1 cells.

Table I

Animal Retroviruses

AIDS-related virus (ARV)
Arian Erthyroblastosis Virus
Avian Leukosis Virus (or Lymphoid Leukosis virus)
Arian Myeloblastosis Virus
Avian Reticuloendotheliosis Virus
Avian Sarcoma Virus
Baboon Endogenous Virus
Bovine Leukemia Virus
Bovine Lentivirus
Bovine Syncytial Virus
Caprine Encephalitis-Arthritis Virus (or Goat Leukoencephalitis Virus)
Arian Myelocytomatosis virus
Corn Snake Retrovirus Chicken Syncytial virus
Duck Infectious Anemia Virus
Deer Kidney Virus
Equine Dermal Fibrosarcoma Virus
Equine Infectious Anemia Virus
Esh Sarcoma Virus Feline Immunodeficiency Virus
Feline Leukemia Virus
Feline Sarcoma Virus
Feline Syncytium-forming virus
Fujinami Sarcoma Virus
Gibbon Ape Leukemia Virus (or Simian Lymphoma Virus or Simian Myelogenous Leukemia Virus)
Golden Pheasant Virus
Human Immunodeficiency Virus 1 (HIV-1)
Human Immunodeficiency Virus 2 (HIV-2)
Human T-Lymphotrophic Virus 1 (HTLV-1)
Human T-Lymphotrophic Virus 2 (HTLV-2)
Human T-Lymphotrophic Virus 3 (HTLV-3)
Lymphoproliferative Disease Virus
Myeloblastosis-associated virus
Myelocytomatosis Virus
Mink Cell Focus-Inducing Virus
Myelocytomatosis Virus 13
Mink Leukemia Virus
Mouse Mammary Tumor Virus
Mason-Pfizer Monkey Virus
Murine Sarcoma Virus
Myeloid Leukemia Virus
Myelocytomatosis Virus
Progressive Pneumonia Virus
Rat Leukemia Virus
Rat Sarcoma Virus
Rous-Associated Virus 0
Rous-Associated Virus 60
Rous-Associated Virus 61
Reticuloendotheliosis-Associated Virus
Reticuloendotheliosis Virus
Reticuloendotheliosis Virus-Transforming
Ring-Necked Pheasant Virus
Rous Sarcoma Virus
Simian Foamy Virus
Simian Immunodeficiency Virus
Spleen Focus-Forming Virus
Squirrel Monkey Retrovirus
Spleen Necrosis Virus
Sheep Pulmonary Adenomatosis/Carcinoma Virus
Simian Sarcoma-Associated Virus (or Wooly Monkey Leukemia Virus)
Simian Sarcoma Virus (or Wooly Monkey Virus)

Table II

Table of Packaging Sequences:
1. Reticuloendotheliosis virus (Rev) *Genome*: Wilhelmsen, et al. *J. Virol.* 52:*172–182* (1984). bases 1–3149; Shimotohno, et al. *Nature* 285:550–554 (1980). bases 3150–3607. *Packaging Sequence (ψ)*:144-base between the Kpn I site at 0.676 kbp and 0.820 kbp relative to the 5I end of the provirus.

J. Embretson and H. Temin *J. Virol.* 61(9):2675–2683 (1987).

2. Human immunodeficiency virus type 1 (HIV-1) *Genome*: Gallo et al. *Science* 224:500–503 (1984) *Packaging Sequence (ψ)*: 19 base pairs between the 5' LTR and the gag gene initiation codon. A. Lever, *J. Virol.* 63(9) 4085–4087 (1989).

3. Moloney murine leukemia virus (Mo-MuLV) *Genome*: Shinnick, et al. *Nature* 293:543–548 (1981). *Packaging sequence (ψ)*:350 nucleotides between the splice site and the AUG site for coding sequence of gag protein. R. Mann, R. Mulligan and D. Baltimore, *Cell* 33:153–159 (1983). *Second packaging sequence (ψ+)*:Only in the 5 half of the U5 region. J. Murphy and S. Goff, *J. Virol.* 63(1):319–327 (1989).

4. Avian sarcoma virus (ASV) *Genome*: Neckameyer and—Wang *J. Virol.* 53:879–884 (1985). Packaging sequence (ψ):150 base pairs between 300 and 600 bases from the left (gag-pol) end of the provirus. P. Shank and M. Linial, *J. Virol.* 36(2):450–456 (1980).

5. Rous sarcoma virus (RSV) *Genome*: Schwartz et al. *Cell* 32:853–869 (1983). *Pakaging Sequence (ψ)*:230 base pairs from 120-base (PB site beginning) to 22-base before gag start codon. S. Kawai and T. Koyama (1984), *J. Virol.* 51:147–153.

6. Bovine leukosis virus (BLV) *Genome*: Couez, et al. *J. Virol.* 49:615–620 (1984), bases 1–341; Rice et al. *Virology* 142:357–377 (1985), bases 1–4680; Sagata et al. *Proc. Natl. Acad. Sci.* 82:677–681 (1985), complete BLV provirus. *Packaging sequence (ψ)*:the present inventors predict that it lies between the end of the primer binding site at about base 340 and the initiation codon for gag at about base 41–8.

REFERENCES

1. Abramova, T. V. et al., (1991) Nucleos. Nucleot. 10, 419.
2. Alford, R. L., Honda, S., Lawrence, C. B. and Belmont, J. W. (1991) RNA secondary structure in Mo-MLV Psi, pp 611–619.
3. Aronoff, R. and Linial, M. (1991) J. Virol. 65, 71–80.
4. Babe, L. M., Pichuantes, S., and Clark, C. S. (1991) Biochemistry 30, 106.
5. Brown, A. M. C. and Scott, M. R. D. (1987) In DNA Cloning, A Practical Approach, Vol. III, pp 189–212.
6. Chang, P. S. et al., (1990), Clin. Biotechnol. 2, 23.
7. Chatterjee, S., Johnson, P. R., and Wong, K. K. Jr. (1992) Science 258, 1485.
8. Chen, C. and Okayama, H. (1987) Mol. Cell. Biol. 7, 2745–2749.
9. Chrisley, L. A. (1991) Antisense Research and Development, 1:65–113.
10. Coffin, J. (1985) In RNA Tumor Viruses, eds. Weis, R., Teich, N., Varmus, .H. and Coffin, J. (Cold Spring Harbor Lab., Cold Spring Harbor, N.Y.), Vol. 2, pp 766–782.
11. Curiel, T. et al. (1992) Hum. Gene Ther. 3, 147.
12. Debouck, C. (1992) Aids Research and Human Retroviruses 8, 153–164.
13. Dropulic, B., Lin, N. H., Martin, M. A. and Jeang, K.-T. (1992) J. Virol. 66, 1432–1441.
14. Egholm, (1992) J. Am. Chem. Soc. 114:1895.
15. Epstein, F. H. (1991) The New England J. Med. 324, 308–317.
16. Freed, E., Delwart, E., Buchschacher, G. Jr., and Panganiban, A., (1992) Proc. Natl. Acad. Sci. U.S.A. 89, 70.
17. Gautsch, J. W. and Meier, H. (1976) Virology 72, 509–513.
18. Goodchild, J. et al., (1988) Proc. Natl. Acad. Sci. U.S.A. 85, 5507.
19. Gordon et al. (1987) Bio/Technology 5:1183.
20. Greene, W. C. (1990) Annu. Rev. Immunol. 8, 453–475.
21. Hammer et al. (1985) Nature 315:680.
22. Hammper, A. et al. (1990) Nucleic Acid Res. 18, 299–304.
23. Han, L., Yun, J. S. and Wagner, T. E. (1991) Proc. Natl. Acad. Sci. U.S.A. 88, 4313–4317.
24. Hanvey et al., (1992) Science Vol. 258:1409–1548.
25. Harrison, G. P. and Lever, A. M. L. (1992) J. Virol. 66, 4144–4153.
26. Haseloff, J. and Gerlach, W. J. (1988) Nature (London) 334, 585–591.
27. Jones, K. A. (1989) The New Biologist 1, 127–135.

28. Kotlin, R. M. et al. (1990) Proc. Natl. Acad. Sci. U.S.A. 87, 2211.
29. Levy, J. A. (1984) Science 225, 840.
30. Levy, J. A. (1993) Microbiological Rev. 57, 183–289.
31. Lo, K. M. S., Blasolo, M. A., Dehni, G., Palu, G. and Haseltine, W. A. (1992) Virology 190, 176–183.
32. Malim, M. H. et al., (1992) J. Exp. Med. 176, 1197.
33. Malim, M. H., Bohnlein, S., Hauber, J., and Cullen, B. R. (1989) Cell 58, 205.
34. Marshall, W. S. and Caruthers, M. H., (1993) Science 259, 1564.
35. McClure, M. O., Moore, J. P., Blanc, D. F., Scotting, P., Cook, G. M. W., Keynes, R. J., Weber, J. N., Davies, D. and Weiss, R. A. (1992) Aids Research and Human Retroviruses 8, 19–26.
36. McCune, J. M. (1991) Cell 64, 351–363.
37. Miller, D. (1992) Nature 357, 455–460.
38. Miller, A. D. (1992) Current Topic in Microbiology and Immunology 158, 1–24.
39. Nielson, (1991) Science 254:1497.
40. Ojwang, J. O., Hampel, A., Looney, D. J., Wong-Staal, F. and Rappaport, J. (1992) Proc. Natl. Acad. Sci. U.S.A. 89, 10802–10806.
41. Perriman, R., Delves, A. and Gerlach, W. L. (1992) Gene 113, 157–163.
42. Peterlin, B. M. and Luciw, P. A. (1988) Bio/Technology 6, 794–799.
43. pittius et al. (1988) PNAS 85:5874.
44. Poznansky, M., Lever, A., Bergeron, L., Haseltine, W., and Sodroski, J. (1991) J. Virol. 65, 532.
45. Pyle, A. M. (1993) Science 261, 709–714.
46. Reed, K. C. and Mann, D. A. (1985) Nucleic Acids Res. 13, 7207–7221.
47. Rossi, J. J., Elkins, D., Zaia, J. A. and Sullivan, S. (1992) In Aids Research and Human Retroviruses 8, 183–189.
48. Rossi, J. J. and Sarver, N., (1992) Innovations in Antiviral Development and the Detection of Virus Infection, 95–109.
49. Saenger, W. (1984) Principles of Nucleic Acid Structure (Springer, N.Y.).
50. Sarver, N., Cantin, E. M., Chang, P. S., Zaia, J. A., Ladne, P. A., Stephens, D. A. and Rossi, J. J. (1990) Science 247, 1222–1225.
51. Sczakiel, G., Oppenländer, M., Rittner, K. and Pawlina, M. (1992) J. Virol. 66, 5576–5581.
52. Simons et al. (1987) Nature 328:530.
53. Simons et al. (1988) Bio/Technology 6:179.
54. Sioud, M. and Drlica, K. (1991) Proc. Natl. Acad. Sci. U.S.A. 88, 7303–7309.
55. Steffy, K. R. and Wong-Staal, F., (1993) J. Virol. 67, 1854.
56. Stevenson, M., Bukrinsky, M. and Haggerry, S. (1992) Aids Research and Human Retroviruses 8, 107–117.
57. Sullenger, B. A., Gallardo, H. F., Ungers, G. E. and Gilboa, E. (1991) J. Virol. 65, 6811.
58. Sullenger, B. A., Gallardo, H. F., Ungers, G. E. and Gilboa, E. (1990) Cell 63, 601–608.
59. Sullenger, B. A. et al. (1993) Science 262, 1567–1569.
60. Teich, N., Wyke, J., Mak, T., Bernstein, A. and Hardy, W. (1985) In RNA Tumor Viruses, eds. Weiss, R., Teich, N., Varmus, H. and Coffin, J. (Cold Spring Harbor Lab., Cold Spring Harbor, N.Y.) Vol. 1, pp 901–923.
61. Trono, D., Feinberg, M., and Baltimore, D., (1989) Cell 59, 113.
62. Uhlmann, E. and Peyman, A., (1990) Antisense Oligonucleotides: A New Therapeutic Principle. Chemical Reviews 90:543–584.
63. Van Brunt, J. Molecular Farming: Transgenic Animals as Bioreactors. Bio/Technology 6:1149–1154.
64. Van der Krol, J., Mol, N., Stuitje, A. R., (1988) Bio-Techniques 6, 958.
65. Warrilow, D., Takayama, Y. and Symonds, G. (1992) BioTechniques 13, 42–43.
66. Weerasinghe, M., Liem, S. E., Asad, S., Read, S. E. and Joshi, S. (1991) J. Virol. 65, 5531–5534.
67. Zuker, M. and Stiegler, P. (1981) Nucleic Acid. Res. 9, 133–148.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:1:

NCUGANGANN NNNNGAAAN  19

( 2 ) INFORMATION FOR SEQ ID NO:2:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( x i ) SEQUENCE DESCRIPTION: SEQ ID NO:2:

NCUGANGANG AAAN  14

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:3:

NGANNGAAAC NNNANANUAC N                                    21

(2) INFORMATION FOR SEQ ID NO:4:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:4:

TTAGGATCCT GATGAGTCCG TGAGGACGAA ACTGGCTC                38

(2) INFORMATION FOR SEQ ID NO:5:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO:5:

CCTAGGCTCT GATGAGTCCG TGAGGACGAA ACTTCCTGTT AGGATCCTGA TGAGTCCGTG    60

AGGACGAAAC TGGCTCGCTA TGTTCTGATG AGTCCGTGAG GACGAAACAC CCAA    114

(2) INFORMATION FOR SEQ ID NO:6:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:6:

GTCAAAAATT GGCGCTGATG AGTCCGTGAG GACGAAACTC ACCAGTCGCC G    51

(2) INFORMATION FOR SEQ ID NO:7:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (xi) SEQUENCE DESCRIPTION: SEQ ID NO:7:

GUGGCGCCCG AACAGGGACG CGAAAGCGAA AGUAGAACCA GAGGAGCUCU CUCGACGCAG    60

GACUCGGCUU GCUGAAGCGC GCACAGCAAG AGGCGAGGGG CGGCGACUGG UGAGUACGCC    120

AAUUUUUGAC UAGCGGAGGC UAGAAGGAGA GAGAGAUGGG UGCGAGAGCG    170

What is claimed:

1. A compound which comprises at least the following sequences:

CCTAGGCTCTGATGAGTCCGTGAGGACGAAACTTCCTGTTAG
GATCCTGATGAGTCCGTGAGGACGAAACTGGCTCGCTATGTT
CTGATGAGTCCGTGAGGACGAAACACCCAA (SEQ. ID. NO.5)

and

-continued

GTCAAAAATTGGCGCTGATGAGTCCGTGAGGACGAAACTCAC
CAGTCGCCA (SEQ. ID. NO.6)

wherein each of T, G, A and C represents a nucleotide and wherein all the sequences are in either a sense or an anti-sense orientation.

2. The RNA encoded by the compound of claim 1.

3. A compound which comprises at least the following sequence:

TTAGGATCCTGATGAGTCCGTGAGGACGAAA-
CTGGCTC    (SEQ ID NO. 4)

wherein each of T, G, A and C represents a nucleotide and wherein the sequence is in either a sense or an anti-sense orientation.

4. The RNA encoded by the compound of claim 3.

5. A compound which comprises at least the following sequence:

CCTAGGCTCTGATGAGTCCGTGAGGACGAAACTTCCTGTTAG
GATCCTGATGAGTCCGTGAGGACGAAACTGGCTCGCTATGTT
CTGATGAGTCCGTGAGGACGAAACACCCAA (SEQ. ID. NO.5)

wherein each of T, G, A and C represents a nucleotide and wherein the sequence is in either a sense or an anti-sense orientation.

6. The RNA encoded by the compound of claim 5.

7. A compound which comprises at least the following sequence:

GTCAAAAATTGGCGCTGATGAGTCCGT-
GAGGACGAAACTCACCAGTC GCCG    (SEQ ID NO. 6)

wherein each of T, G, A and C represents a nucleotide and wherein the sequence is in either a sense or an anti-sense orientation.

8. The RNA encoded by the compound of claim 7.

* * * * *